United States Patent
O'Mahony et al.

(10) Patent No.: US 9,259,019 B2
(45) Date of Patent: Feb. 16, 2016

(54) BIFIDOBACTERIUM STRAIN

(75) Inventors: Liam O'Mahony, Cork (IE); Barry Kiely, Cork (IE)

(73) Assignees: Mars, Incorporated, McLean, VA (US); Alimentary Health Ltd., Cork (IE)

( * ) Notice: Subject to any disclaimer, the term of this patent is extended or adjusted under 35 U.S.C. 154(b) by 0 days.

(21) Appl. No.: 13/468,512

(22) Filed: May 10, 2012

(65) Prior Publication Data

US 2013/0004540 A1  Jan. 3, 2013

Related U.S. Application Data

(63) Continuation of application No. PCT/IE2010/000067, filed on Nov. 11, 2010.

(51) Int. Cl.
| | |
|---|---|
| *C12N 1/20* | (2006.01) |
| *A61P 29/00* | (2006.01) |
| *A61P 1/12* | (2006.01) |
| *A61P 37/06* | (2006.01) |
| *A61P 37/02* | (2006.01) |
| *A61K 35/74* | (2015.01) |
| *A61P 1/00* | (2006.01) |
| *A23K 1/00* | (2006.01) |
| *A23L 1/30* | (2006.01) |
| *C12R 1/01* | (2006.01) |
| *A23K 1/16* | (2006.01) |
| *A23K 1/18* | (2006.01) |

(52) U.S. Cl.
CPC ............... *A23K 1/009* (2013.01); *A23K 1/164* (2013.01); *A23K 1/1846* (2013.01); *A23L 1/3014* (2013.01); *A61K 35/74* (2013.01); *C12R 1/01* (2013.01); *A23Y 2300/55* (2013.01)

(58) Field of Classification Search
None
See application file for complete search history.

(56) References Cited

U.S. PATENT DOCUMENTS

| | | |
|---|---|---|
| 2004/0265279 A1 | 12/2004 | Dinan et al. |
| 2005/0069505 A1* | 3/2005 | Breton et al. ................. 424/59 |
| 2005/0175598 A1 | 8/2005 | Boileau et al. |
| 2010/0183559 A1 | 7/2010 | Van Sinderen et al. |

OTHER PUBLICATIONS

Imaoka, et al., Anti-inflammatory activity of probiotic Bifidobacterium: Enhancement of IL-10 production in peripheral blood mononuclear cells from ulcerative colitis patients and inhibition of I L-8 secretion in HT-29 cells, World Journal of Gastroenterology, vol. 14, No. 16, Apr. 28, 2008, pp. 2511-2516.

Medina, et al., Differential immunomodulatory properties of Bifidobacterium longum strains: relevance to probiotic selection and clinical applications, 2007 British Society for Immunology, Clinical and Experimental Immunology, vol. 150, No. 3, Dec. 2007, pp. 531-538.

PCT International Search Report, mailed Mar. 23, 2011, 6 pages.

* cited by examiner

*Primary Examiner* — Robert A Zeman

(57) ABSTRACT

*Bifidobacterium* strain AH121A is significantly immunomodulatory following oral consumption. The strain is useful as an immunomodulatory biotherapeutic agent.

11 Claims, 39 Drawing Sheets

BIFIDOBACTERIUM STRAIN

CROSS REFERENCE TO RELATED APPLICATION

This application is a continuation application of prior International Application No. PCT/IE2010/000067 filed on Nov. 11, 2010 (aka P-225& WO) which claims the benefit of U.S. application Ser. No. 12/616,752 (aka 11484M) filed Nov. 11, 2009.

INTRODUCTION

The invention relates to a *Bifidobacterium* strain and its use as a probiotic bacteria in particular as an immunomodulatory biotherapeutic agent.

The defense mechanisms to protect the human gastrointestinal tract from colonization by intestinal bacteria are highly complex and involve both immunological and non-immunological aspects (1). Innate defense mechanisms include the low pH of the stomach, bile salts, peristalsis, mucin layers and anti-microbial compounds such as lysozyme (2). Immunological mechanisms include specialized lymphoid aggregates, underlying M cells, called peyers patches which are distributed throughout the small intestine and colon (3). Luminal antigens presented at these sites result in stimulation of appropriate T and B cell subsets with establishment of cytokine networks and secretion of antibodies into the gastrointestinal tract (4). In addition, antigen presentation may occur via epithelial cells to intraepithelial lymphocytes and to the underlying lamina propria immune cells (5). Therefore, the host invests substantially in immunological defense of the gastrointestinal tract. However, as the gastrointestinal mucosa is the largest surface at which the host interacts with the external environment, specific control mechanisms must be in place to regulate immune responsiveness to the 100 tons of food which is handled by the gastrointestinal tract over an average lifetime. Furthermore, the gut is colonized by over 500 species of bacteria numbering $10^{11}$-$10^{12}$/g in the colon. Thus, these control mechanisms must be capable of distinguishing non-pathogenic adherent bacteria from invasive pathogens, which would cause significant damage to the host. In fact, the intestinal flora contributes to defense of the host by competing with newly ingested potentially pathogenic microorganisms.

It is believed by some that probiotic bacteria are more effective when derived from the species, or closely related species, intended to be treated. Therefore, there is a need for probiotic strains derived from companion animals to be used for companion animals that are different to those derived from humans.

WO 01/90311 discloses probiotic micro-organisms isolated from faecal samples obtained from cats having probiotic activity. However, these bacteria were obtained from faecal samples, and may not form part of the natural intestinal microflora present in the upper portion of the GI tract.

Consequently, there is a need to provide strains of bacteria obtainable by isolation from the natural intestinal microflora present in the upper portion of the GI tract that are particularly adapted for cats, and have been selected for their probiotic properties and ability to survive processing, and to incorporate these strains into compositions that are suitable for their use.

STATEMENTS OF INVENTION

According to the invention, there is provided an isolated strain of *Bifidobacterium* NCIMB 41675.

The *Bifidobacterium* strain may be in the form of viable cells, the *Bifidobacterium* strain may be in the form of non-viable cells.

The *Bifidobacterium* may be isolated from colonic biopsy tissue from a feline subject.

The *Bifidobacterium* strain may be significantly immunomodulatory following oral consumption.

The invention also provides a formulation which comprises a *Bifidobacterium* strain as described herein.

The formulation may further comprise a probiotic material. The formulation may further comprise a prebiotic material. The formulation may further comprise an ingestable carrier. The ingestible carrier may be a pharmaceutically acceptable carrier such as a capsule, tablet or powder.

The ingestible carrier may be a food product such as an oil suspension, a milk based suspension, cheese, a cocoa butter based composition, a gravy and/or a yoghurt based composition.

The invention further provides a foodstuff which comprises a *Bifidobacterium* strain or a formulation as described herein.

The foodstuff may be a dry foodstuff. The foodstuff may be a wet foodstuff. The foodstuff may further comprise a probiotic material. The foodstuff may further comprise a prebiotic material. The foodstuff may be a companion animal food.

The invention also provides a *Bifidobacterium* strain, or a formulation, or a foodstuff as described herein for use as a medicament.

The invention also provides a *Bifidobacterium* strain, or a formulation, or a foodstuff as described herein for use in the prophylaxis and/or treatment of undesirable inflammatory activity.

The invention also provides a *Bifidobacterium* strain, or a formulation, or a foodstuff as described herein for use in the prophylaxis and/or treatment of undesirable gastrointestinal inflammatory activity.

The invention also provides a *Bifidobacterium* strain, or a formulation, or a foodstuff as described herein for use in the prophylaxis and/or treatment of auto-immune disorders due to undesirable inflammatory activity.

The invention also provides a *Bifidobacterium* strain, or a formulation, or a foodstuff as described herein for use in the prophylaxis and/or treatment of diarrhoeal disease due to undesirable inflammatory activity.

The invention also provides a *Bifidobacterium* strain, or a formulation, or a foodstuff as described herein for use in the regulation of or improvement of the immune system of companion animals.

The invention also provides a *Bifidobacterium* strain, or a formulation, or a foodstuff as described herein for use in the prophylaxis and/or treatment of autoimmune disease in companion animals.

The invention also provides a *Bifidobacterium* strain, or a formulation, or a foodstuff as described herein for use in the prophylaxis and/or treatment of inflammation in companion animals.

We describe a *Bifidobacterium* strain AH121A (NCIMB 41675) or mutants or variants thereof.

The strain may be obtainable by isolation from resected and washed feline gastrointestinal tract.

The mutant may be a genetically modified mutant. The variant may be a naturally occurring variant of *Bifidobacterium*.

The strain may be a probiotic. It may be in the form of a biologically pure culture.

Also described is an isolated strain of *Bifidobacterium* NCIMB 41675.

*Bifidobacterium* strains may be in the form of viable cells. Alternatively *Bifidobacterium* strains may be in the form of non-viable cells.

The general use of probiotic bacteria may be in the form of viable cells. However, it may also be extended to non-viable cells such as killed cultures or compositions containing beneficial factors expressed by the probiotic bacteria. This may include thermally killed micro-organisms or micro-organisms killed by exposure to altered pH or subjection to pressure. With non-viable cells product preparation may be simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

We also describe uses of the bacteria obtainable by isolation from resected and washed feline gastrointestinal tract for maintaining and improving companion animal health, and compositions comprising the lactic acid bacteria.

We describe a formulation which comprises the *Bifidobacterium* strain described herein, the formulation may include another probiotic material, the formulation may include a prebiotic material.

*Bifidobacterium* are commensal microorganisms. They have been isolated from the microbial flora within the human gastrointestinal tract. The immune system within the gastrointestinal tract cannot have a pronounced reaction to members of this flora, as the resulting inflammatory activity would also destroy host cells and tissue function. Therefore, some mechanism(s) exist whereby the immune system can recognize commensal non-pathogenic members of the gastrointestinal flora as being different to pathogenic organisms. This ensures that damage to host tissues is restricted and a defensive barrier is still maintained.

Throughout the specification the terms mutant, variant and genetically modified mutant include a strain of Bifidobacteria whose genetic and/or phenotypic properties are altered compared to the parent strain. Naturally occurring variant of *Bifidobacterium longum* includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a Bifidobacteria strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain of Bifidobacteria that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of Bifidobacteria can be identified by DNA sequence homology analysis with the parent strain. Strains of Bifidobacteria having a close sequence identity with the parent strain are considered to be mutant or variant strains. A Bifidobacteria strain with a sequence identity (homology) of 96% or more, such as 97% or more, or 98% or more, or 99% or more with the parent DNA sequence may be considered to be a mutant or variant. Sequence homology may be determined using on-line homology algorithm "BLAST" program, publicly available at http://www.ncbi.nlm.nih.gov/BLAST/.

Mutants of the parent strain also include derived Bifidobacteria strains having at least 85% sequence homology, such as at least 90% sequence homology, or at least 95% sequence homology to the 16s-23s intergenic spacer polynucleotide sequence of the parent strain. These mutants may further comprise DNA mutations in other DNA sequences in the bacterial genome.

BRIEF DESCRIPTION OF THE DRAWINGS

The invention will be more clearly understood from the following description thereof given by way of example only with reference to the accompanying drawings in which; —

DETAILED DESCRIPTION OF THE INVENTION

Figure 1:
FIG. 1 is a photograph of *B. longum* AH121A grown on a Congo Red Agar plate.

A deposit of *Bifidobacterium longum* strain AH121A was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41675.

A deposit of *Bifidobacterium longum* strain UCC 35624 was made at the National Collections of Industrial and Marine Bacteria Limited (NCIMB) Ferguson Building, Craibstone Estate, Bucksburn, Aberdeen, AB21 9YA, Scotland, U K on Jan. 13, 1999, and accorded the accession number NCIMB 41003.

The *Bifidobacterium longum* may be a genetically modified mutant or it may be a naturally occurring variant thereof.

Preferably the *Bifidobacterium longum* is in the form of viable cells.

Alternatively the *Bifidobacterium longum* may be in the form of non-viable cells.

As used herein, "companion animal" means a domestic animal. Preferably, "companion animal" means a domestic feline (cat), canine (dog), rabbit, ferret, horse, cow, or the like. More preferably, "companion animal" means a domestic feline.

Lactic Acid Bifidobacteria Strains

The first aspect of the present invention comprises a strain of lactic acid bacteria of the genus Bifidobacteria obtainable by isolation from resected and washed feline gastrointestinal tract having probiotic activity in animals. Probiotics are microorganisms, either viable or dead, processed compositions of micro-organisms, their constituents such as proteins or carbohydrates, or purified fractions of bacterial ferments that beneficially affect a host. The general use of probiotic bacteria is in the form of viable cells. However, it can be extended to non-viable cells such as killed cultures or compositions containing beneficial factors expressed by the probiotic bacteria. This may include thermally killed micro-organisms, or micro-organisms killed by exposure to altered pH or subjected to pressure. For the purpose of the present invention, "probiotics" is further intended to include the metabolites generated by the micro-organisms of the present invention during fermentation, if they are not separately indicated. These metabolites may be released to the medium of fermentation, or they may be stored within the micro-organism. As used herein "probiotic" also includes bacteria, bacterial homogenates, bacterial proteins, bacterial extracts, bacterial ferment supernatants, and mixtures thereof, which perform beneficial functions to the host animal when given at a therapeutic dose.

It has been found that lactic acid bacteria of the genus Bifidobacteria obtainable by isolation directly from resected and washed GI tract of mammals are adherent to the GI tract following feeding of viable bacterial cells, and are also significantly immunomodulatory when fed to animals in viable, non-viable or fractionated form. Without being bound by theory, it is believed that Bifidobacteria obtainable by isolation from resected and washed GI tract closely associate with the gut mucosal tissues. Without further being bound by theory, this is believed to result in the probiotic Bifidobacteria of the present invention generating alternative host responses that result in its probiotic action. It has been found that probiotic bacteria obtainable by isolation from resected and washed GI tract can modulate the host's immune system via direct interaction with the mucosal epithelium, and the host's immune cells. This immunomodulation, in conjunction with the traditional mechanism of action associated with probiotic bacteria, i.e. the prevention of pathogen adherence to the gut by occlusion and competition for nutrients, results in the Bifidobacteria of the present invention being highly efficacious as a probiotic organism.

The *Bifidobacterium* of the present invention, obtainable by isolation from resected and washed feline GI tract, has in vitro anti-microbial activity against a number of pathogenic bacterial strains/species. Without being bound by theory, it is believed that this in vitro anti-microbial activity is indicative of potential probiotic activity in vivo in animals, preferably companion animals such as felines. The lactic acid bacteria of the present invention preferably have in vitro anti-microbial activity against *Salmonella typhimurium*, *Listeria monocytogenes*, *Listeria innocua* or *Eschericia coli*, more preferably a mixture of these strains, more preferably still, all of these strains.

Without being bound by theory, it is believed that the anti-microbial activity of the lactic acid bacteria of the present invention may be the result of a number of different actions by the lactic acid bacteria herein. It has previously been suggested in the art that several strains of bacteria isolated from faecal samples exert their probiotic effect in the GI tract following oral consumption by preventing the attachment of pathogenic organisms to the gut mucosa by occlusion. This requires oral consumption of "live" or viable bacterial cells in order for a colony of bacteria to be established in the gut. However, it is believed that the Bifidobacteria of the present invention, obtainable by isolation from resected and washed feline GI tract, whilst exerting some probiotic effect due to occlusion if given in a viable form, may deliver a substantial probiotic effect in either the viable or non-viable form due to the production during fermentation in vitro of a substance or substances that either inhibit the growth of or kill pathogenic microorganisms, and/or alter the host animal's immune competence. This form of probiotic activity is desirable, as the bacteria of the present invention can be given as either viable or non-viable cultures or purified fermentation products and still deliver a beneficial therapeutic effect to the host animal.

Preferably, the lactic acid bacteria of the present invention are able to maintain viability following transit through the GI tract. This is desirable in order for live cultures of the bacteria to be taken orally, and for colonisation to occur in the intestines and bowel following transit through the oesophagus and stomach. Colonisation of the intestine and bowel by the lactic acid bacteria of the present invention is desirable for long-term probiotic benefits to be delivered to the host. Oral dosing of non-viable cells or purified isolates thereof induces temporary benefits, but as the bacteria are not viable, they are not able to grow, and continuously deliver a probiotic effect in situ. As a result this may require the host to be dosed regularly in order to maintain the health benefits. In contrast, viable cells that are able to survive gastric transit in the viable form, and subsequently colonise by adhering to and proliferating on the gut mucosa are able to deliver probiotic effects continuously in situ. Therefore, it is preferable that the lactic acid bacteria of the present invention maintain viability after suspension in a media having a pH of 2.5 for 1 hour. As used herein, "maintain viability" means that at least 25% of the bacteria initially suspended in the test media are viable using the plate count method known to those skilled in the art. Preferably, "maintain viability" means that at least 50% of the bacteria initially suspended are viable. It is desirable for the lactic acid bacteria of the present invention to maintain viability following exposure to low pH as this mimics the exposure to gastric juices in the stomach and upper intestine in vivo following oral consumption in animals.

The strain of lactic acid bacteria of the genus Bifidobacteria obtainable by isolation from resected and washed feline gastrointestinal tract can be used to deliver probiotic benefit following oral consumption in animals, preferably companion animals or humans. This probiotic benefit generally maintains and improves the overall health of the animal. Non-limiting elements of animal health and physiology that benefit, either in therapeutically relieving the symptoms of, or disease prevention by prophylaxis include inflammatory disorders, immunodeficiency, inflammatory bowel disease, irritable bowel syndrome, cancer (particularly those of the gastrointestinal and immune systems), diarrhoeal disease, antibiotic associated diarrhoea, appendicitis, autoimmune disorders, multiple sclerosis, Alzheimer's disease, amyloidosis, rheumatoid arthritis, arthritis, joint mobility, diabetes mellitus, insulin resistance, bacterial infections, viral infections, fungal infections, periodontal disease, urogenital disease, surgical associated trauma, surgical-induced metastatic disease, sepsis, weight loss, weight gain, excessive adipose tissue accumulation, anorexia, fever control, cachexia, wound healing, ulcers, gut barrier infection, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, and epidermal disorders, Preferred are treatment of the gastrointestinal tract, including treatment or prevention of diarrhoea; immune system regulation, preferably the treatment or prevention of autoimmune disease and inflammation; maintaining or improving the health of the skin and/or coat system, preferably treating or preventing atopic disease of the skin; ameliorating or reducing the effects of aging, including mental awareness and activity levels; preventing disorders associated with the hypothalamus-pituitary-adrenal axis, and improving joint health whereby improving mobility.

The treatment of the disorders disclosed above may be measured using techniques known to those skilled in the art. For example, inflammatory disorders including autoimmune disease and inflammation may be detected and monitored using in vivo immune function tests such as lymphocyte blastogenesis, natural killer cell activity, antibody response to vaccines, delayed-type hypersensitivity, and mixtures thereof. Such methods are briefly described herein, but well known to those skilled in the art.

1. Lymphocyte blastogenesis: This assay measures the proliferative response in vitro of lymphocytes isolated from fresh whole blood of test and control animals to various mitogens and is a measure of overall T- and B-cell function. Briefly, peripheral blood mononucleocytes (PBMC) are isolated from whole blood by Ficoll-Hypaque density centrifugation methods known to those skilled in the art. The isolated PBMCs are washed twice in RPMI 1640 cell media supplemented with HEPES, L-glutamine and penicillin/streptomycin. The washed cells are resuspended in RPMI 1640, counted, and the cell density adjusted appropriately. The $2 \times 10^5$ cells are exposed to a range of concentrations (0.1 μg/ml to 100 μg/ml) of various mitogens, some examples of which include pokeweed mitogen (Gibco), phytohaemagglutinin (Gibco) and conconavalin A (Sigma) in triplicate for 72 hours at 37° C. and 5% $CO_2$ with 10% foetal bovine serum (Sigma). At 54 hours the cells are pulsed with 1μCi H-thymidine, and the cells harvested and scintillation counts read on a TopCount NXT at 72 hours.

2. Natural killer cell activity: As described in U.S. Pat. No. 6,310,090, this assay measures the in vitro effector activity of natural killer cells isolated from fresh whole blood of test and control animals. Natural killer cells are a component of the innate immune function of a mammal. Feline thyroid adenocarcinoma cells were used as target cells in assessing N K cell cytotoxic activity. This cell line was previously shown to be susceptible to killing by feline N K cell. Target cells were cultured in a T75 flask with 20 mL minimum essential medium (MEM; Sigma Chem. Co., St. Louis, Mo.) supplemented with 10% fetal calf serum (FCS), 100 U/mL of penicillin and 100 μg/mL of streptomycin. When confluent, target cells were trypsinized, washed 3 times and resuspended to $5 \times 10^5$ cells/mL in complete medium (RPMI-1640+10% FCS+100 U/mL of penicillin+100 μg/mL of streptomycin). Triplicate 100 μL aliquots of the target cells were pipetted into 96-well U-bottom plates (Costar, Cambridge, Mass.) and incubated for 8 hours to allow cell adherence. Lymphocytes (effector cells; 100 μL) isolated by Ficoll-Hypaque separation (as described above) were then added to the target cells to provide an effector/target cell (E:T) ratio of 10:1. After 10 hours of incubation at 37° C., 20 μl of a substrate containing 5. μg of 3-(4,5-dimethylthiazol-2-yl)-2,5-diphenyltetrazolium bromide (MTT) was added. The mixture was incubated for 4 hours at 37° C. after which the unmetabolized MTT was removed by aspiration. The formazan crystals were dissolved by adding 200 μL of 95% ethanol. Optical density was measured at 570 nm using a microplate reader. The percentage of NK cell-specific lysis was calculated as follows: Specific Cytotoxicity (%)=100×{1−[(OD of target cells and effector cells−OD of effector cells)/(OD of target cells)]}

3. Antibody response to vaccines: The test subjects are given an array (up to 5) of vaccines after at least 12 weeks of probiotic or control feeding. The vaccines may be a mixture of novel and redundant vaccines. Non-limiting examples of vaccine arrays that may be used include mixtures of vaccines prepared by Fort Dodge Animal Health. Non-limiting examples of vaccines suitable for use herein include Feline distemper, adenovirus, coronavirus, parainfluenza, and parvovirus. The test subject's vaccine history will determine the vaccines to be used. The specific antibodies to the vaccines given are measured in blood for 3 weeks and the length and strength of response in control and probiotic feeding groups compared. 4. Delayed-type hypersensitivity: An in vivo, non-invasive method of assessing immune system status. This test comprises an intradermal injection of the polyclonal mitogen Phytohemmaglutinin (PHA) in combination with sheep red blood cells a multivalent vaccine, histamine (100 μL of 0.0275 g/L Histamine Phosphate; Greer, Lenoir, N C) or PBS (100 μL of Phosphate Buffered Saline, 8.5 g/L; Sigma). The immune response to the antigen is recorded as skinfold thickness using calipers at time intervals of 0, 24, 48 and 72 hours post-injection. An increase in skinfold thickness is indicative of a greater hypersensitivity response that should be decreased by treatment with the bacteria of the present invention.

Additional methods for determining the effect of the Bifidobacteria bacteria of the present invention are described in U.S. Pat. Nos. 6,133,323 and 6,310,090.

Furthermore, ameliorating the effects of age may be determined using dual x-ray absorptometry or CT scan for measuring body composition, including body fat mass, fat-free mass and bone mineral content. Similarly, this method may be used to determine anatomy changes such as weight loss or bone density in subjects following infection.

The Bifidobacteria of the present invention may also be used in a method for reducing stress levels in companion animals. Concentrations of blood stress hormones including epinephrine, norepinephrine, dopamine, Cortisol, C-reactive protein and other acute phase proteins may be measured to determine stress levels and their reduction or maintenance. These hormones are recognized biomarkers of stress and can be readily measured using techniques known to those skilled in the art. Additionally, direct measure of adrenal size as an in vivo marker of activity of the hypothalamus-pituitary-adrenal axis may be measured by C T imaging.

Further still, maintenance or improvement of the health of the skin and/or coat system of companion animals, including atopic disease of the skin, may be measured using skin and coat assessments conducted by two trained individuals. Examples of criteria examined during such assessments include: a) Shedding index: A shedding index is assigned to each test subject by collecting hair produced during a standardized brushing session. The hair is retained and weighed, and control and test subjects compared. b) Subjective skin/coat evaluations: Trained panelists subjectively evaluate skin and coat condition by assessing shedding, dander, shine, uniformity, softness and density. c) Skin functional assessment: The barrier function of the skin may be assessed by wiping the skin surface with an acetone-soaked gauze. This technique effectively disrupts the skin barrier by removing single cell layers and associated lipid fractions of the stratum corneum. Barrier disruption is quantified by measuring the increase in transepidermal water loss (TEWL) and the degree of redness of the insulted site using methods known to those skilled in the art. Redness (erythema) scores are obtained using the previously described camera and lighting system. TEWL readings and redness scores are obtained immediately before and after disruption, and at five and 24-hour endpoints to assess the protective and healing properties of skin.

Furthermore, the treatment of gastrointestinal infection in companion animals may comprise improving microbial ecology of companion animals. Improving the microbial ecology of companion animals preferably comprises reducing the levels of pathogenic bacteria in the faeces of companion animals. The levels of pathogenic bacteria present in the faeces of companion animals may be enumerated using the standard plate count method known to those skilled in the art. More preferably, the pathogenic bacteria are selected from the group consisting of *Clostridia, Escherichia, Salmonella, bacteriodes* and mixtures thereof. Non-limiting examples of suitable strains of pathogenic bacteria include *C. perfringens, C. difficile, Eschericia coli, Salmonella typhimurium* and mixtures thereof.

The method of use of the bacteria of the present invention may also include the treatment, either prophylactic or therapeutic of the urinary tract of mammals, preferably companion animals. Non-limiting examples of urinary tract treatment include treatment or prevention of urinary tract infections, treatment or prevention of kidney disease, including urinary tract stones, treatment or prevention of bladder infections and the like. Without being bound by theory, it is believed that the Bifidobacteria bacteria of the present invention are useful in preventing these ailments as a result of their ability to degrade oxalic acid, as demonstrated in vitro. Oxalic acid is a by-product of urinary metabolism that can form insoluble precipitates that result in kidney, bladder and other urinary tract infections. By degrading oxalic acid, and therefore potentially preventing its precipitation and build up in the urinary tract, the bacteria of the present invention may treat and prevent infections and other ailments of the urinary tract. Oxalic acid degradation may be measured in vitro using the Oxalic acid test kit cat #755699 commercially available from Boehringer Mannheirn/R-Biopharm.

The Bifidobacteria of the present invention may be used in a method for improving or maintaining the health of companion animals comprising improving fibre digestion. Improving fibre digestion is desirable as it promotes the growth of said probiotic bacteria, as well as beneficial endogenous microflora, which aid in the suppression of some potentially pathogenic bacteria. In addition, a decrease in the amount of toxic metabolites and detrimental enzymes that result from colonic fermentation has been documented in humans (6). Fibre digestion may be determined using the method described in Vickers et al. (7), with the exception that instead of inoculating using diluted fecal samples each experiment used pure cultures of the bacterial strains of interest.

The feline probiotic strains of the present invention may be used to reduce the odor of the feces and urine and concomitantly in the litterbox by reducing the production of compounds in the feces and urine that cause odor. Non-limiting examples of odor-causing compounds include ammonia, indoles, phenols, amines, branched chain fatty acids, and volatile sulphur-containing compounds. Without wishing to be bound by theory it is believed that reducing the levels of these compounds in the feces or urine of a companion animal reduces the odor associated with the feces or urine. Furthermore, for companion animals that use a litter box, there is a concomitant decrease in litter box odor.

The method of use of the lactic acid bacteria of the present invention typically involves oral consumption by the animal. Oral consumption may take place as part of the normal dietary intake, or as a supplement thereto. The oral consumption typically occurs at least once a month, preferably at least once a week, more preferably at least once per day. The lactic acid bacteria of the present invention may be given to the companion animal in a therapeutically effective amount to maintain or improve the health of the animal, preferably a companion animal. As used herein, the term "therapeutically effective amount" with reference to the lactic acid bacteria, means that amount of the bacteria sufficient to provide the desired effect or benefit to a host animal in need of treatment, yet low enough to avoid adverse effects such as toxicity, irritation, or allergic response, commensurate with a reasonable benefit/risk ratio when used in the manner of the present invention. The specific "therapeutically effective amount" will vary with such factors as the particular condition being treated, the physical condition of the user, the duration of the treatment, the nature of concurrent therapy (if any), the specific dosage form to be used, the carrier employed, the solubility of the dose form, and the particular dosing regimen.

Preferably, the lactic acid bacteria are given to the companion animal at a dose of from $1.0E+04$ to $1.0E+14$ CFU per day, more preferably from $1.0E+06$ to $1.0E+12$ CFU per day. The composition preferably may contain at least 0.001% of from $1.0E+04$ to $1.0E+12$ CFU/g of the lactic acid bacteria of the genus Bifidobacteria obtainable by isolation from resected and washed feline GI tract. The lactic acid bacteria can be given to the animal in either viable form, or as killed cells, or distillates, isolates or other fractions of the fermentation products of the lactic acid bacteria of the present invention, or any mixture thereof.

Preferably, the lactic acid bacteria, or a purified or isolated fraction thereof, are used to prepare a composition intended to maintain or improve the health of an animal. As indicated above, the composition may be part of the normal dietary intake, or a supplement. Where the composition comprises part of the normal dietary intake, the composition may be in the form of a dried animal food such as biscuits or kibbles, a processed grain feed, a wet animal food, yoghurts, gravies, chews, treats and the like.

Such compositions may comprise further components. Other components are beneficial for inclusion in the compositions used herein, but are optional for purposes of the invention. For example, food compositions are preferably nutritionally balanced. In one embodiment, the food compositions may comprise, on a dry matter basis, from about 20% to about 50% crude protein, preferably from about 22% to about 40% crude protein, by weight of the food composition. The crude protein material may comprise any material having a protein content of at least about 15% by weight, non-limiting examples of which include vegetable proteins such as soybean, cotton seed, and peanut, animal proteins such as casein, albumin, and meat tissue. Non-limiting examples of meat tissue useful herein include fresh meat, and dried or rendered meals such as fish meal, poultry meal, meat meal, bone meal and the like. Other types of suitable crude protein sources include wheat gluten or corn gluten, and proteins extracted from microbial sources such as yeast.

Furthermore, the food compositions may comprise, on a dry matter basis, from about 5% to about 35% fat, preferably from about 10% to about 30% fat, by weight of the food composition. Further still, food compositions comprising the lactic acid bacteria of the present invention may also comprise from about 4% to about 25% total dietary fibre. The compositions may also comprise a multiple starch source as described in WO99/51108.

The compositions of the present invention may further comprise a source of carbohydrate. Grains or cereals such as rice, corn, milo, sorghum, barley, alfalfa, wheat, and the like are illustrative sources. In addition, the compositions may also contain other materials such as dried whey and other dairy by products.

The compositions comprising the bacteria of the present invention may also comprise a prebiotic. "Prebiotic" includes substances or compounds that are fermented by the intestinal flora of the companion animal and hence promote the growth or development of lactic acid bacteria in the gastro-intestinal tract of the companion animal at the expense of pathogenic bacteria. The result of this fermentation is a release of fatty acids, in particular short-chain fatty acids in the colon. This has the effect of reducing the pH value in the colon. Non-limiting examples of suitable prebiotics include oligosaccharides, such as inulin and its hydrolysis products commonly known as fructooligosaccharides, galacto-oligosaccharides, xylo-oligosaccharides or oligo derivatives of starch. The prebiotics may be provided in any suitable form. For example, the prebiotic may be provided in the form of plant material which contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti S A of Tirlemont 3300, Belgium under the trade mark "Raftiline". For example, the inulin may be provided in the form of Raftiline (g) ST which is a fine white powder which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti S A of Tirlemont 3300, Belgium under the trade mark "Raftilose". For example, the inulin may be provided in the form of Raftilose (g) P95. Otherwise, the fructooligosaccharides may be obtained by hydrolyzing inulin, by enzymatic methods, or by using micro-organisms.

For dried companion animal foods a suitable process is extrusion cooking, although baking and other suitable processes may be used. When extrusion cooked, the dried companion animal food is usually provided in the form of a kibble. If a prebiotic is used, the prebiotic may be admixed with the other ingredients of the dried companion animal food prior to processing. A suitable process is described in European patent application No 0850569. If a probiotic micro-organism is used, the organism is best coated onto or filled into the dried companion animal food. A suitable process is described in European patent publication Number E P 0 862 863.

For wet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. Typical wet food compositions may comprise from about 5% to about 15% protein, from about 1% to about 10% fat, and from about 1% to about 7% fibre. Non-limiting ingredients that may be used in wet food compositions include chicken, turkey, beef, whitefish, chicken broth, turkey broth, beef broth, chicken liver, brewers rice, corn grits, fish meal, egg, beet pulp, chloride, flax meal, lamb, beef byproducts, chicken by-products and mixtures thereof. In another embodiment, supplement compositions such as biscuits, chews, and other treats may comprise, on a dry matter basis, from about 20% to about 60% protein, or from about 22% to about 40% protein, by weight of the supplement composition. As another example, the supplement compositions may comprise, on a dry matter basis, from about 5% to about 35% fat, or from about 10% to about 30% fat, by weight of the supplement composition. Food and supplement compositions intended for use by felines or felines are commonly known in the art.

The companion animal foods may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids and docosahexanoic acid.

Borage oil, blackcurrent seed oil and evening primrose oil are suitable sources of gamma linolenic acid. Safflower oils, sunflower oils, corn oils and soy bean oils are suitable sources of linoleic acid. These oils may also be used in the coating substrates referred to above. Zinc may be provided in various suitable forms, for example as zinc sulfate or zinc oxide. Further, many ingredients commonly used in companion animal foods are sources of fatty acids and zinc. It has been observed that the combination of chicory, as a source of prebiotic, with a linoleic-acid rich oil, such as soy bean oil, provides unexpected benefits, suggestive of a synergistic effect.

Where the composition is in the form of a gravy, the composition preferably comprises at least 10% of a broth, or stock, non-limiting examples of which include vegetable beef, chicken or ham stock. Typical gravy compositions may comprise from about 0.5% to about 5% crude protein, from about 2% to about 5% crude fat, and from about 1% to about 5% fibre.

Further non-limiting examples of supplements suitable for use herein include powders, oil suspensions, milk-based suspensions, cheeses, cocoa-butter-based compositions and pills or capsules. Where the composition is in the form of a pill, suitable binding agents are required to maintain the pill in a solid, pressed form. Non-limiting examples of suitable binding agents include the natural gums such as xanthan gum, pectins, lecithins, alginates and others known to those skilled in the art. Where the composition is in the form of a capsule, the composition is preferably encapsulated using technologies known to those skilled in the art. Non-limiting examples of suitable encapsulation materials include polyvinyl alcohol (PVA), polyvinylpyrrolidone (PVP), alginates, and gelatin. Yoghurt-based compositions may comprise from about 1% to about 5% protein, from about 10% to about 20% carbohydrate, from about 1% to about 5% fibre, from about 1% to about 5% fat and from about 50% to about 90% liquid carrier such as milk.

EXAMPLES

The following examples are provided to illustrate the invention and are not intended to limit the scope thereof in any manner.

Example 1

Isolation of *Bifidobacterium longum* AH121A

*Bifidobacterium longum* strain AH121a was isolated from feline bowel tissue.

Feline intestinal samples were obtained from healthy cats presenting at the local veterinarians for owner initiated and approved euthanasia. All animals were healthy and disease-free. The colon, mid-colon, caecum and ileum of each cat were dissected in order to expose the mucosa.

Supernatants were removed following agitation of the mucosal tissue (vortexed for 1 minute) and following mechanical homogenisation of the tissue. Each supernatant was plated on de Mann Rogosa Sharpe (MRS) agar. These were incubated anaerobically, using the Anerocult GasPak system, for 48 hours at 37° C. Isolated colonies from the plates were re-streaked onto either MRS and again grown anaerobically under the same conditions. Isolated colonies were re-streaked a further 4 times in order to purify a single strain. Colony morphology and microscopic appearance were assessed. Suitable isolates were tested for Gram reaction and catalase activity. Identification of gram positive, catalase negative rods was performed using API testing (API 5 OCHL, BioMerieux). Harvested cells were washed twice with 0.05M phosphate buffer (pH 6.5) and cysteine-HCl (500 mg/L) followed by sonication. Centrifugation removed cellular debris. Supernatants were incubated with NaF (6 mg/ml) and Na iodoacetate (10 mg/ml) for 30 minutes at 37° C. The reaction was stopped by incubation with hydroxylamine HCl (pH6.5) for 10 minutes at room temperature. Colour development was monitored following the addition of HCl (4M), $FeCl_3.6H_2O$ (5% (w/v) in 0.1M HCl) and fructose-6-phosphate (Na salt). Formation of acetyl phosphate from fructose-6-phosphate was evidenced by the reddish colour formed by the ferric chelate of its hydroxymate.

Species Identification 16s intergenic spacer (IGS) sequencing was performed to identify the species of bifidobacteria isolated. Briefly, DNA was isolated from AH121A using 100 µl of Extraction Solution and 25 µl of Tissue Preparation solution (Sigma, XNAT2 Kit). The samples were incubated for 5 minutes room temperature, followed by 2 hrs at 95° C. then 100 µl of Neutralization Solution (XNAT2 kit) was added. Genomic DNA solution was quantified using a Nanodrop spectrophotometer and stored at 4° C. PCR was performed using the IGS primers, IGS L: 5'-GCTGGATCACCTCCTTTCT-3' (SEQ ID NO. 3) which resulted in the identification of SEQ ID NO. 1 and IGS R: 5'-CTGGTGCCAAGGCATCCA-3' (SEQ ID NO. 4) which resulted in the identification of SEQ ID NO. 2. The cycling conditions were 94° C. for 3 min (1 cycle), 94° C. for 30 sec, 53° C. for 30 sec, 72° C. for 30 sec (28 cycles). The PCR reaction contained 4 µl (50 ng) of DNA, PCR mix (XNAT2 kit), 0.4 µM IGS L and R primer (MWG Biotech, Germany). The PCR reactions were performed on an Eppendorf thermocycler. The PCR products (10 µl) were run alongside a molecular weight marker (100 bp Ladder, Roche) on a 2% agarose EtBr stained gel in TAE, to determine the IGS profile. PCR products of *Bifidobacterium* (single band) were purified using the Promega Wizard PCR purification kit. The purified PCR products were sequenced using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/). The nearest match to the sequence was identified and then the sequences were aligned for comparison using DNASTAR MegAlign software. The sequences (SEQ ID NO. 1 [IGS forward sequence] and SEQ ID NO. 2 [IGS reverse sequence]) obtained can be viewed in the sequence listing. Searching the NCIMB database revealed that AH121A has a unique IGS (SEQ ID NO. 1 [forward sequence] and SEQ ID NO. 2 [reverse sequence]) sequence with its closest sequence homology to a *Bifidobacterium longum*.

Example 2

Congo Red Agar Screen

A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Strains that produce less EPS take up the Congo red stain easily, resulting in a pink/red colony morphology. Strains that do not produce an EPS stain red and look almost transparent in the red agar background.

Referring to FIG. 1 the colony morphology for *B. logum* AH121A is convex, mucoid, bright white colonies.

Example 3

To determine the resistance of feline bacterial isolate AHF121A to various concentrations of porcine bile and to assess the survival of feline bacterial isolate AHF121A at pH 2.5 for 6 hours and subsequent bile resistance using various concentrations of bile.

Experimental Design:

The test strain was AHF121A *Bifidobacterium longum*. Resistance to bile is examined using MRS/RCA agar plates supplemented with porcine bile (0.3, 0.5, 1.0, 2.0, 5.0, 7.5 and 10%). The survival of the strains at pH 2.5 is monitored at intervals of −5, 5, 30, 60, 120, 180 and 360 min using the plate count method. The bile resistance is examined after challenging the strains at pH 2.5 for 6 h.

Method:

The procedure for the determination of feline bile resistance is outlined below.

An assessment of the survival rate of freeze dried bacteria in the presence of various concentrations of feline bile, ranging from 0.3% to 10%, was carried out.

Synthetic feline bile plates of various concentrations were prepared by making a 45% stock solution of synthetic bile, heat treating the bile stock at 80° C. for 10 min to kill any vegetative cells.

The various concentrations of bile used were:
2%=6.67 ml bile stock+143.33 appropriate agar
1%=3.33 ml bile stock+146.67 ml agar
0.5%=1.67 ml bile stock+148.33 ml agar For each dilution, unwanted molten agar was removed after autoclaving and replaced with the appropriate volume of bile stock.

Bile plates were made fresh daily, but can be stored for up to one week.

The CFU/g of each freeze-dried test stain was quantified via the spread plating technique.

Test strains were spotted on porcine bile plates by resuspending $10^9$ CFU/ml of freeze-dried strains into 10 ml sterile PBS, dividing the porcine bile plates into ¼, and spoting 4 strains (10 µL)/plate.

The plates were dried on the bench for 30 min (or until the spot had dried into the agar) and incubated under appropriate conditions.

The procedure to assess the survival rates of bacterial strains in a low pH environment (pH 2.5) is outlined below.

Enumeration of freeze-dried powders was carried out using the spread plate technique. The Media was acidified by adding 6 M HCl to 100 ml broth adjust to pH 2.5. The volume required to make adjustment was recorded and using sterile techniques the pH of 4×100 ml MRS broth (remaining broth) was adjusted using the same volume of acid. The CFU/g of each freeze-dried test stain was quantified using the spread plate technique $10^9$ CFU/ml of freeze dried bacteria were resuspended into acidified media and incubated under appropriate anaerobic conditions. Survival was measured by removing aliquots at 5, 30, 60, 120, 180, 240 and 360 min and determining the CFU/ml using the spread plate technique.

Results:

TABLE 1

Growth of bacterial isolates in the presence of feline bile

| Strain | % (w/v) Porcine bile | | | |
|---|---|---|---|---|
| | 0.0 | 0.5 | 1.0 | 2.0 |
| AHF121A | +++ | +++ | +++ | ++ |

+++ = very good growth ~100%
++ = good growth ~66%

Figure 3:
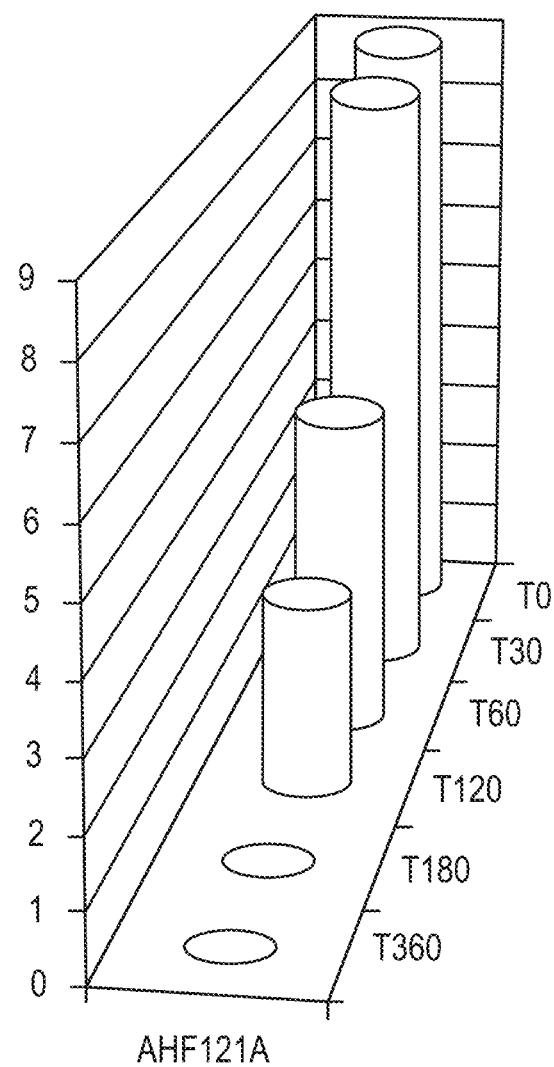
FIG. 3 is a plot illustrating the survival of strain 121A in a low pH environment. Strains were challenged at pH2.5 for 6 hours and their survival assessed using plate counts.

Conclusions:
Table 1 demonstrates the effect of feline bile on the growth of the strain. The feline bacterial strain was able to tolerate ≤2% feline bile concentrations.
FIG. 3 shows acid tolerance at pH 2.5.

Example 4

Effect of 121A on IL-10: IL-12 Ratio

Peripheral blood mononuclear cells (PBMCs) were isolated from healthy human peripheral blood using BD Vacutainer CPT tubes (BD catalog 362761), as per the manufacturer's instructions. PBMCs were washed and resuspended in Dulbecco's Modified Eagle Medium-Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs were incubated ($2\times10^5$ cells per well) in flat-bottomed 96-well plates and 20 µL of a bacterial suspension (at a concentration of $1\times10^7$ CFU/mL) was added. PBMCs were co-incubated with bacteria for 48 hours at 37° C./5% $CO_2$ in an incubator. After the 2 day incubation period, the plates were centrifuged at 300×g, and the supernatants were removed and stored frozen at −80° C. until analysis. Interleukin-10 (IL-10) and Interleukin-12p70 (IL-12p70) levels in the culture supernatants were quantified using a 96-well assay kit from Meso Scale Discovery (Gaithersburg, Md.; catalog K15008B-1)

Bacteria were prepared for co-culture experiments in two formats. (a) Freshly grown bacteria were grown in Difco MRS media and harvested just after entering into stationary phase. All cells were grown under anaerobic conditions at 37° C. (b) Bacteria were grown under anaerobic conditions at 37° C. in Difco MRS media and harvested just after entering into stationary phase. Freeze dried powders were generated for each of these bacteria and stored at −80° C. in pre-aliquoted 100 mg vials. Immediately prior to their use, one aliquot of each strain was removed from the freezer and allowed to reach room temperature. Each strain was washed 3 times in 10 ml ringers followed by centrifugation. A fresh vial was used on each occasion. Growth curves (OD vs number of live cells) were constructed for each growth condition, and washed cells were normalized by cell number before addition to the PBMCs. A no-bacteria control was also included in all experiments. All assays were done in triplicate.

Figure 2:
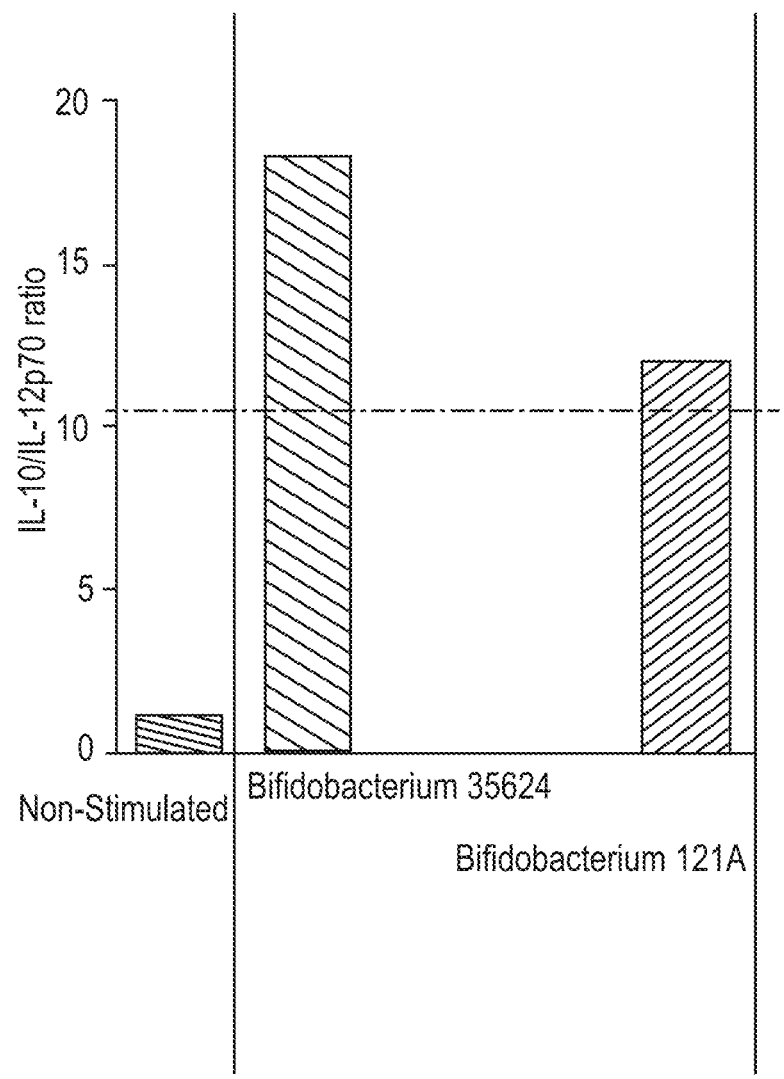
FIG. 2 is a bar chart illustrating the IL-10:IL-12p70 ratio for PBMCs stimulated with *Bifidobacterium longum* strain 121A (Bifidobacterium 121A)

FIG. 2 illustrates the effect of strain 121A on IL-10:IL-12 induction. Both freshly grown and freeze-dried cultures exhibited a similar effect.

Example 5

Effect of 121A on IL-10 Secretion

The appropriate immune response to microbes in an important determinant of overall host health. Excessive responses can lead to inflammatory diseases (e.g. colitis) while inadequate responses lead to pathogen persistence and dissemination. The immunological assays described herein are well described in the literature as useful methods for the determination of host immunological activity in response to encounter with specific microbes.

Human peripheral blood mononuclear cells (PBMCs—contains monocytes, dendritic cells, B cells and T cells) were obtained from healthy volunteers and stimulated in vitro with each bacterial strain. Culture supernatants were then removed and cytokine levels quantified.

IL-10 is a very important cytokine for controlling aberrant pro-inflammatory immune responses. IL-10 knock-out animals develop colitis and gastrointestinal tumours while regulatory cells within the immune system secrete and utilize IL-10 in order to control potentially damaging immune responses. Thus, enhanced secretion of this cytokine would be protective against inappropriate inflammatory activity and excessive immune responses to pathogens.

Figure 5:
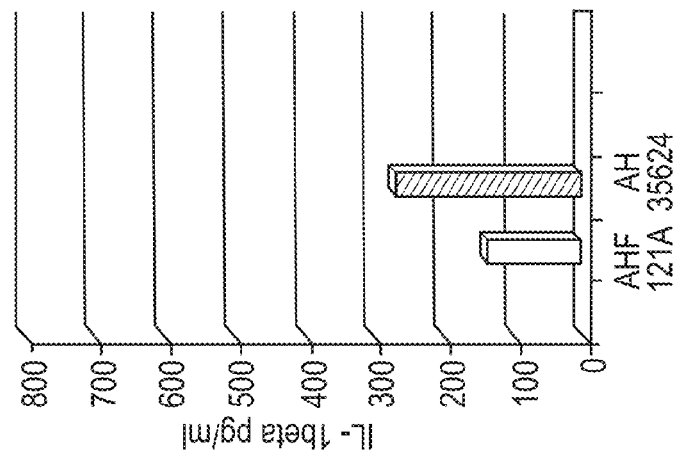
FIGS. 4 to 6 are plots of cytokine secretions from in vitro cultured peripheral blood mononuclear cells (PBMCs)
Figure 4:
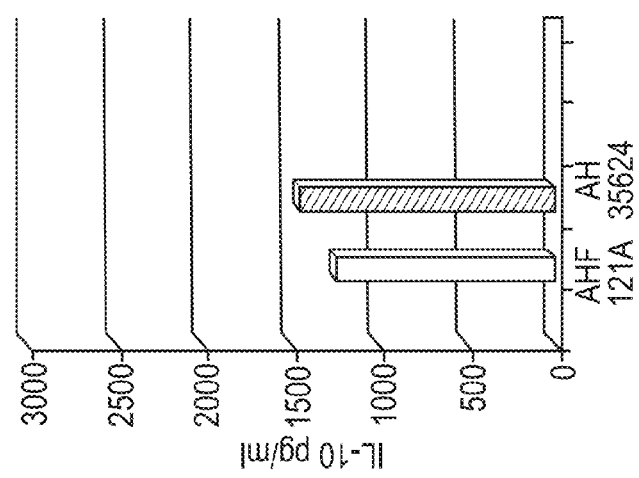
Figure 6:
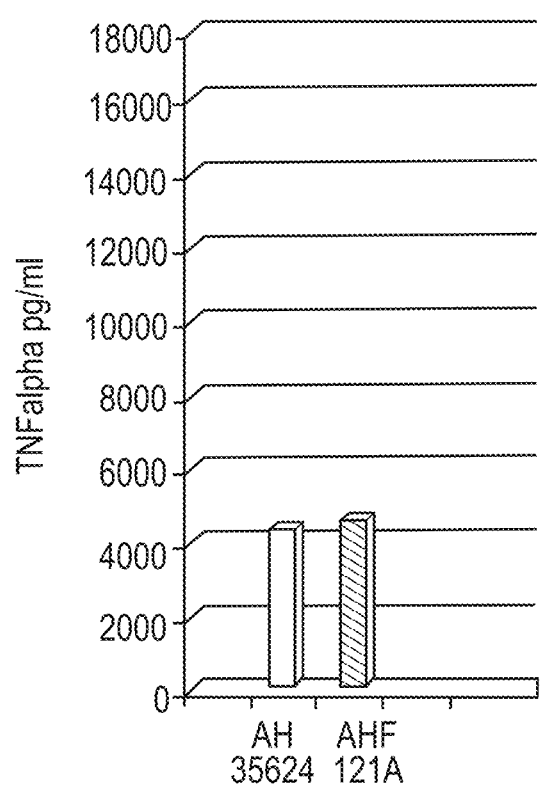
Figure 7A:
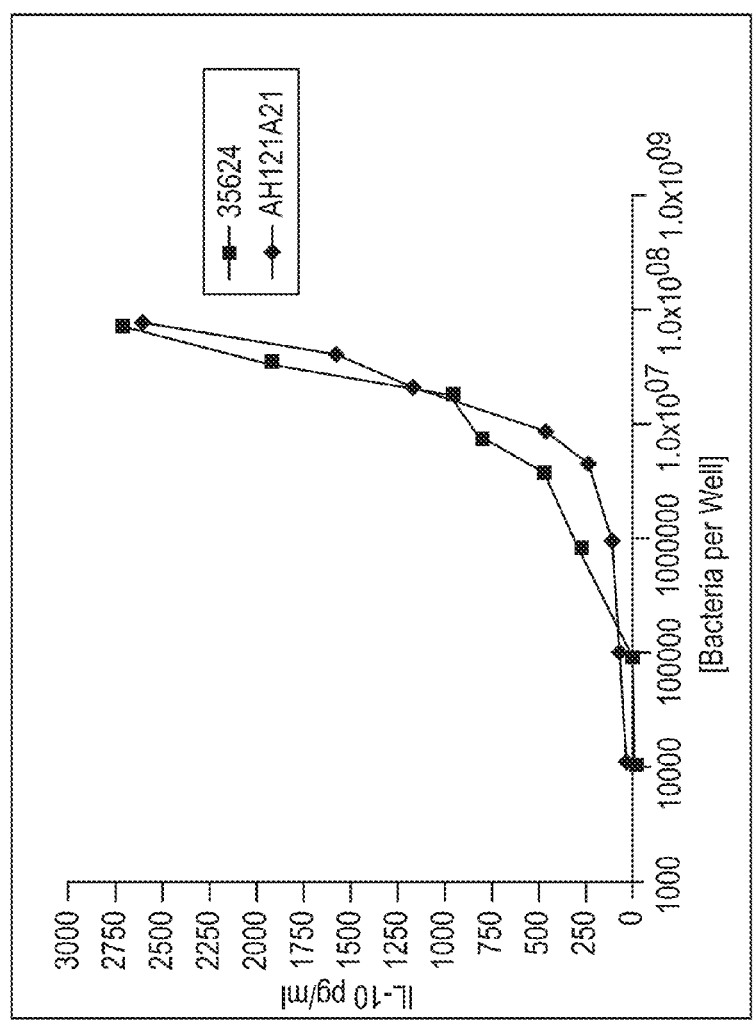
FIG. 7 A to E are line graphs showing the induction profile of IL-10 in PBMC after in vitro stimulation with increasing concentrations of 121A and Bif 35624.
Figure 7B:
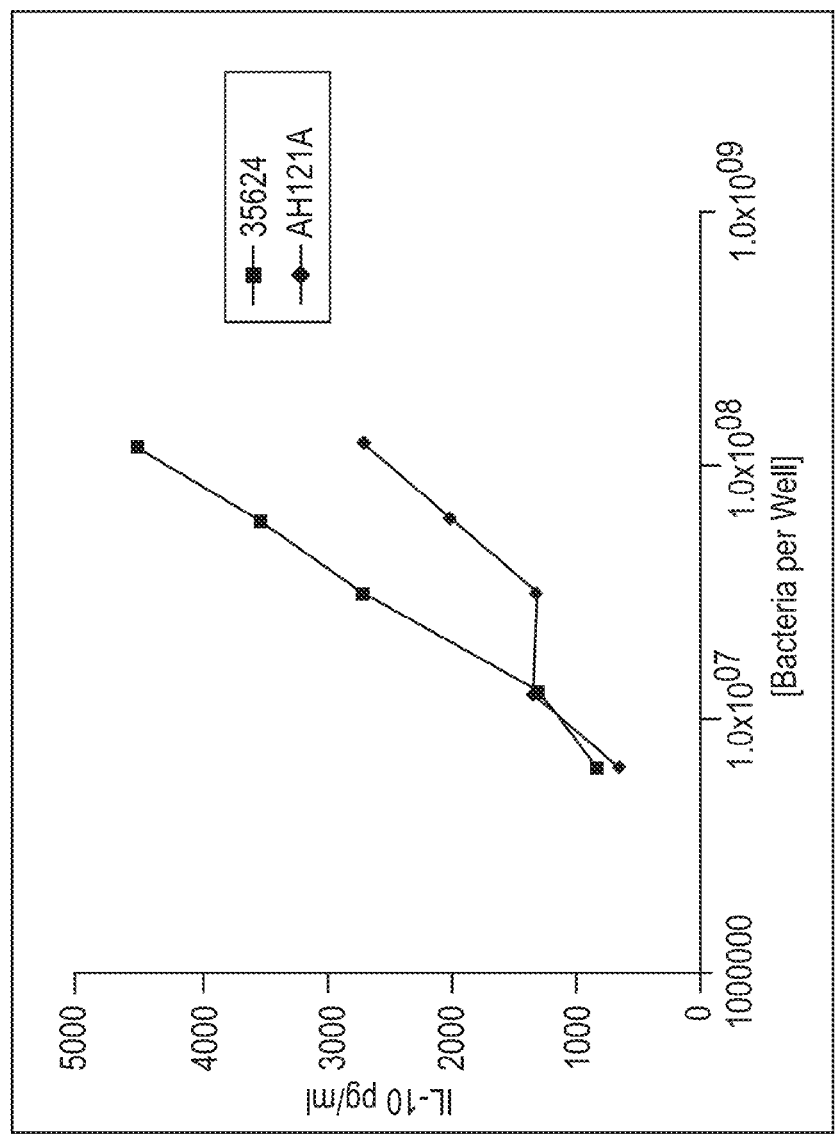
Figure 7C:
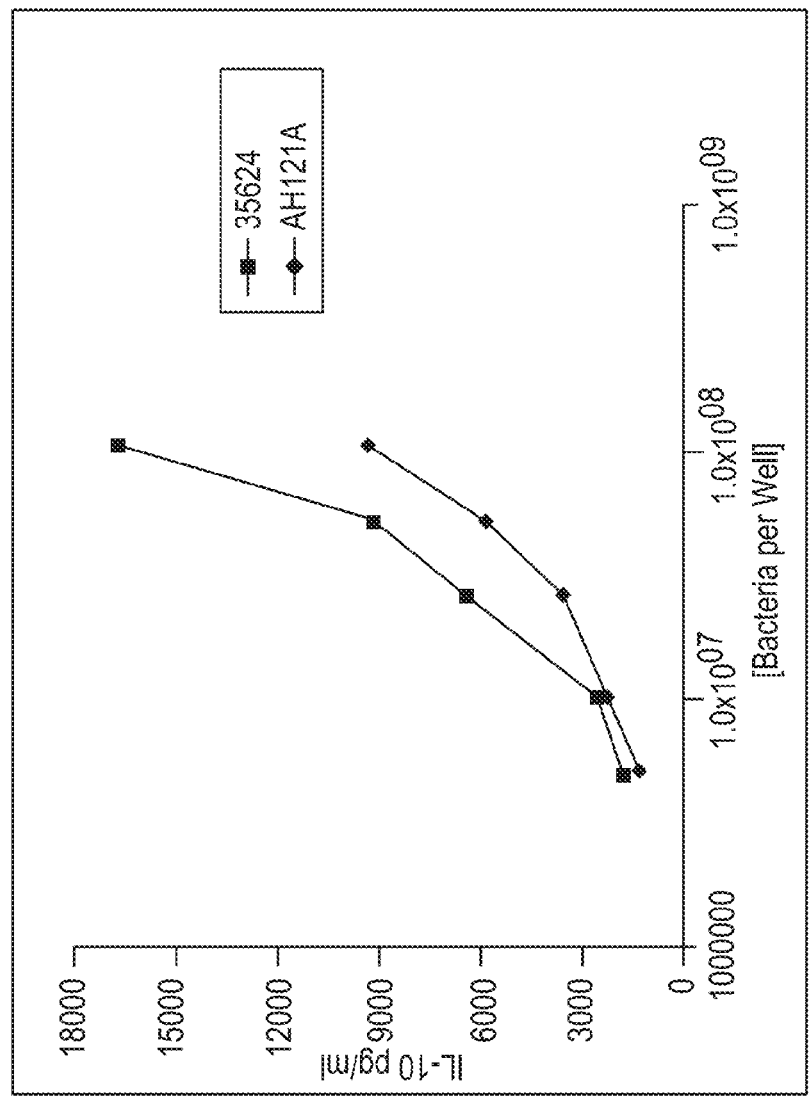
Figure 7D:
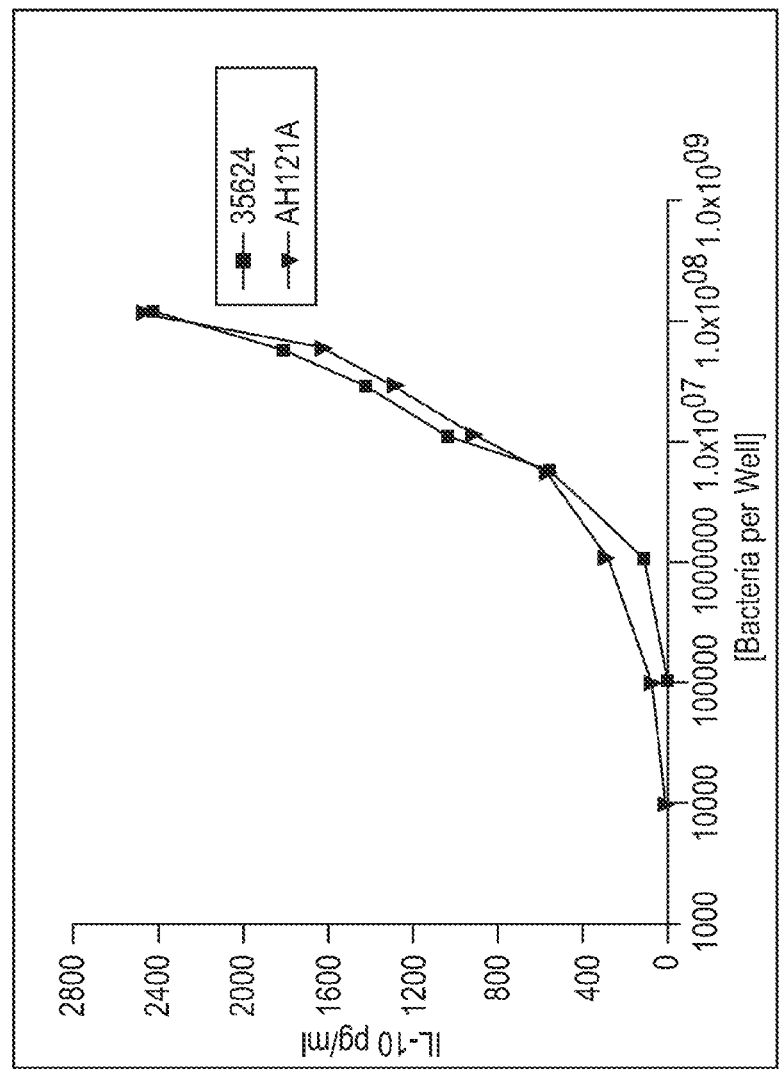
Figure 7E:
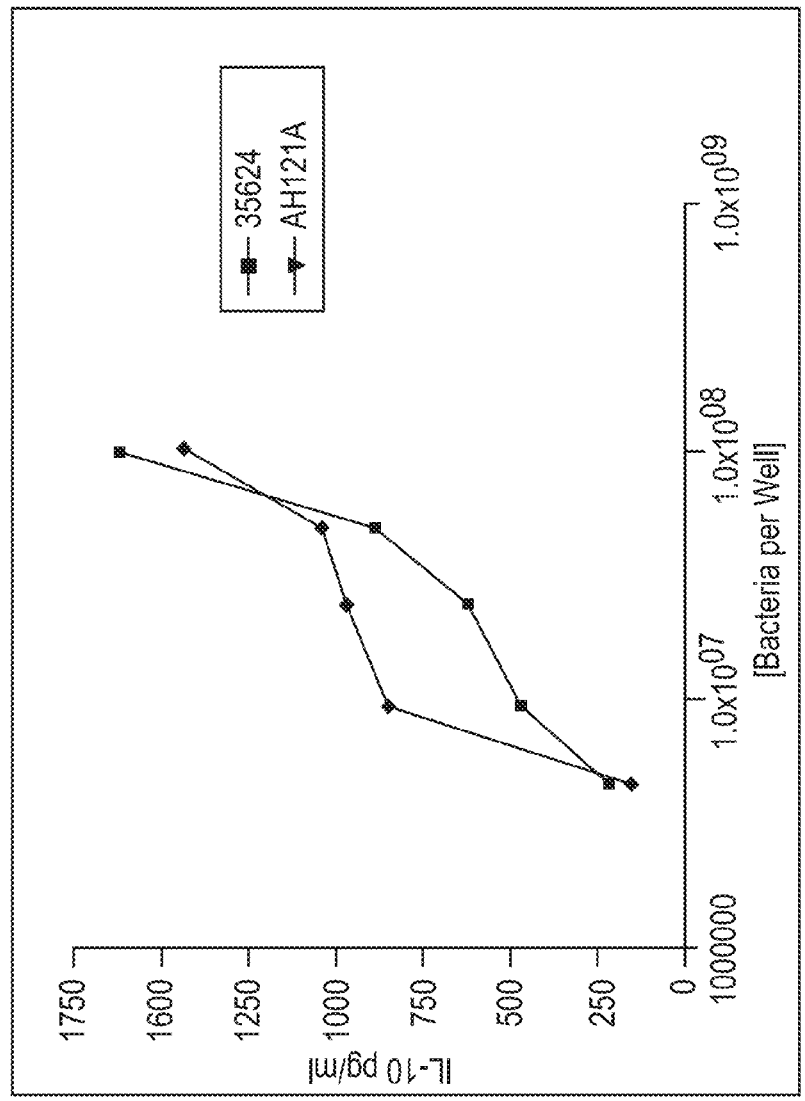
Figure 8A:
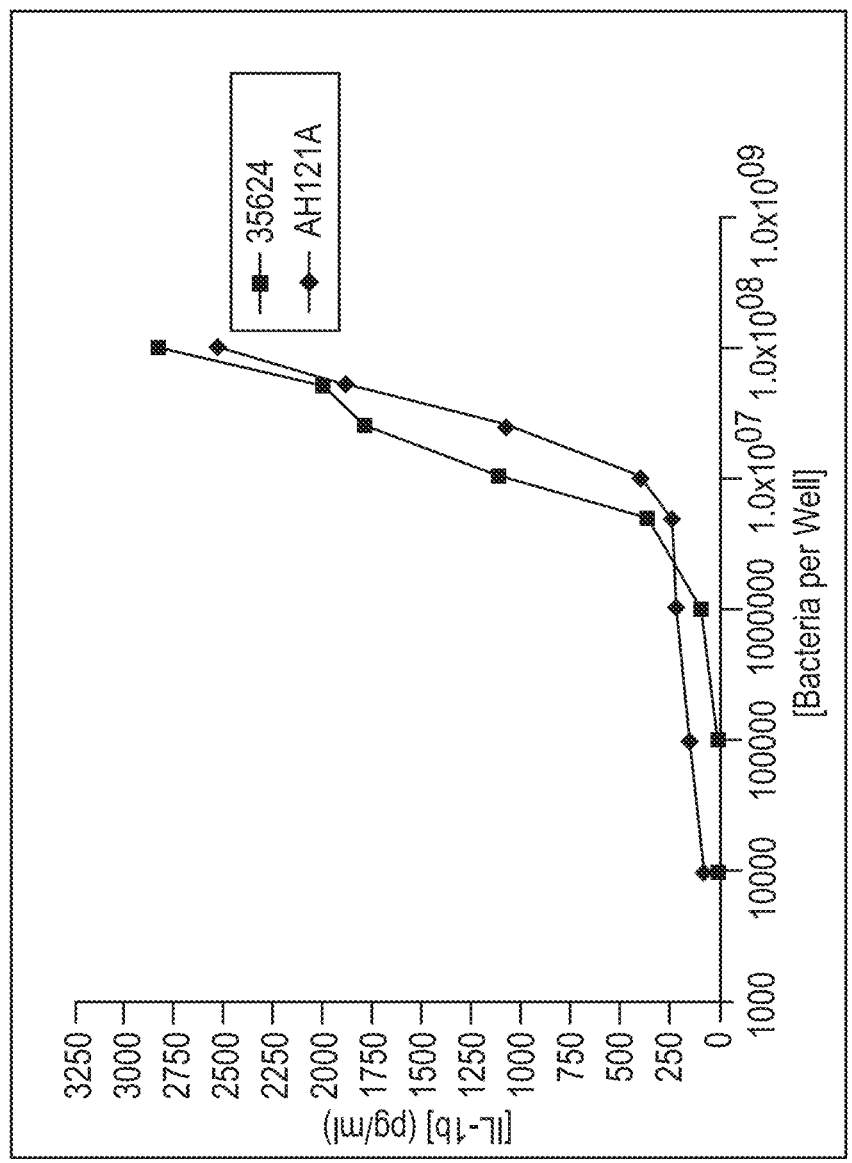
FIG. 8 A to D are line graphs showing the induction profile of IL-1β in PBMC after in vitro stimulation with increasing concentrations of 121A and Bif 35624.
Figure 8B:
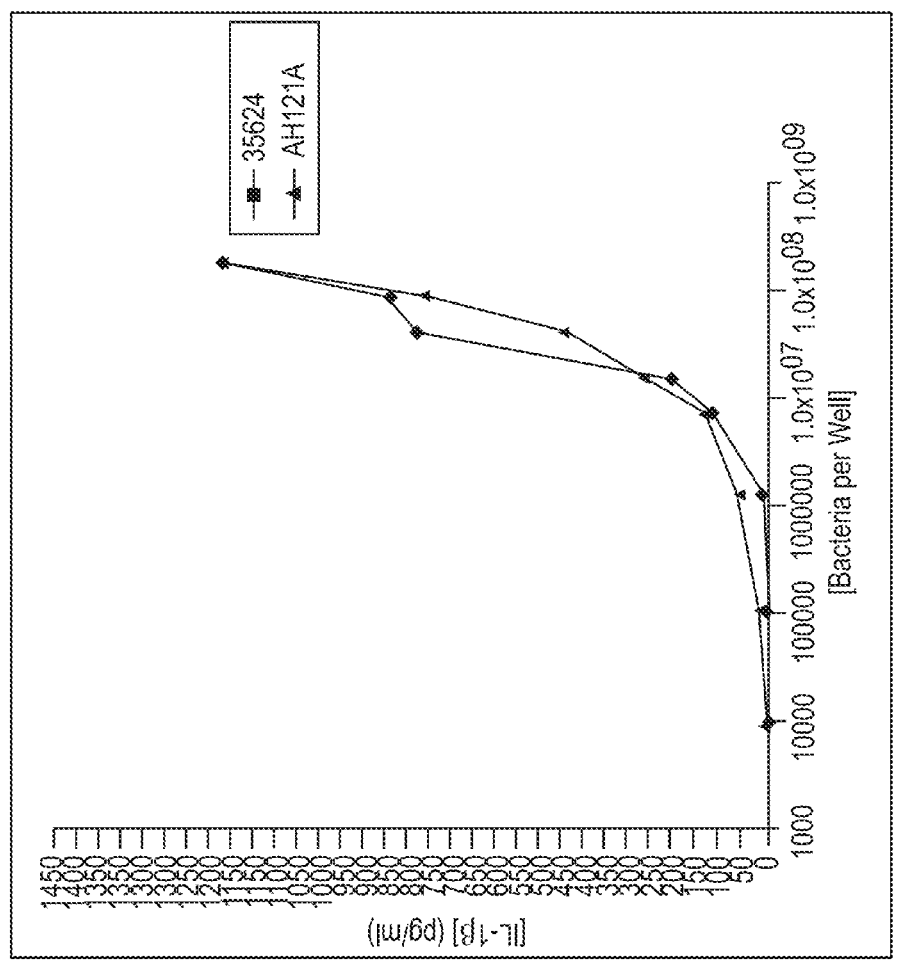
Figure 8C:
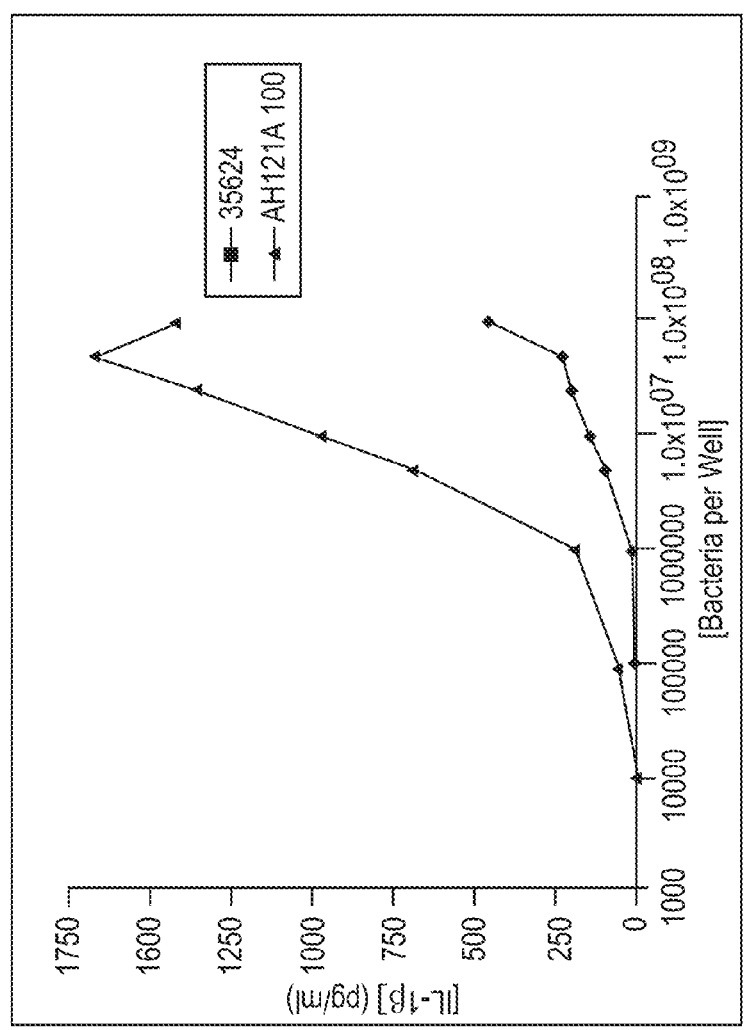
Figure 8D:
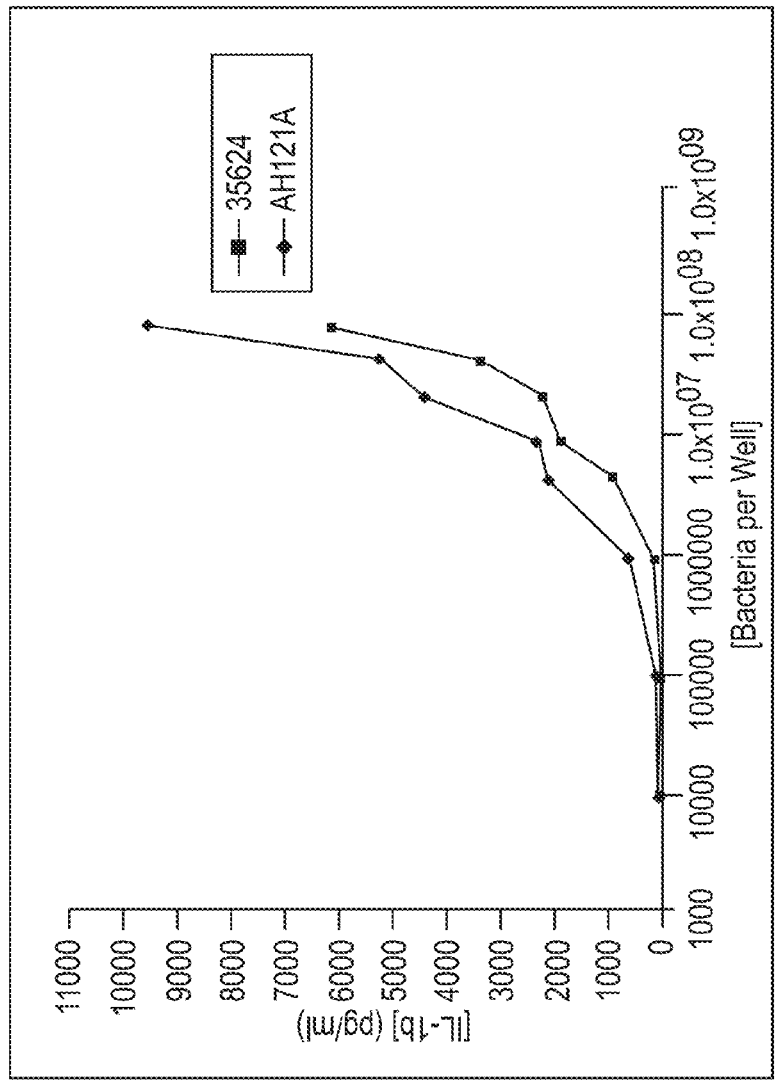
Figure 9A:
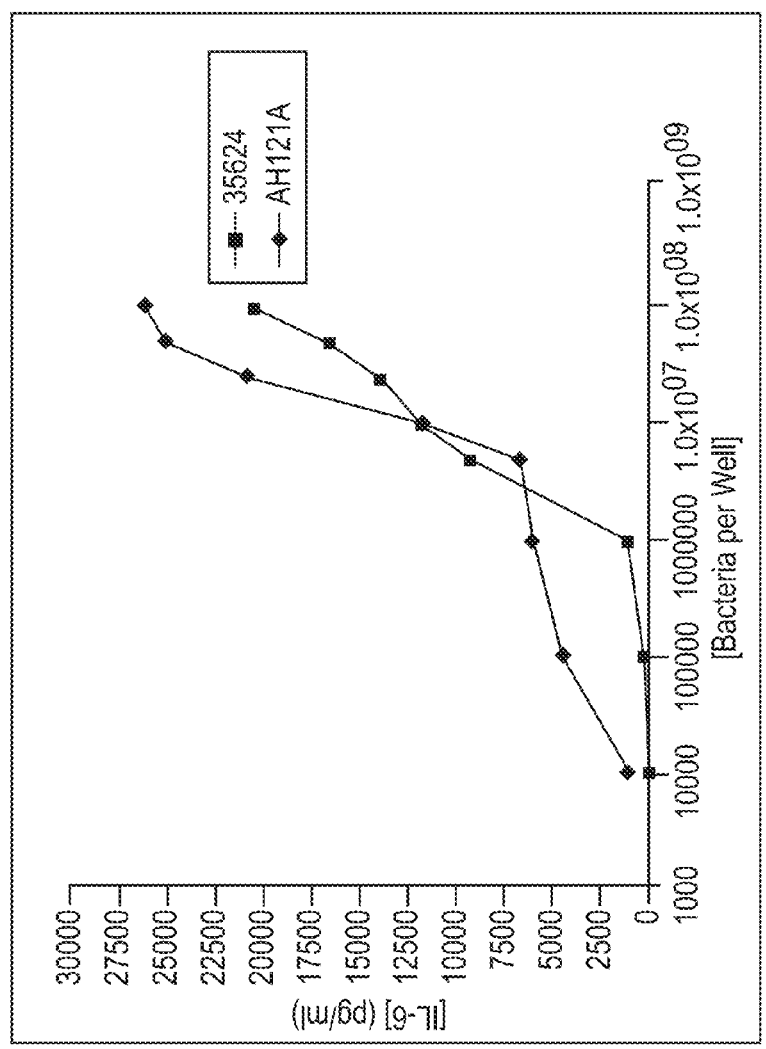
FIG. 9 A to D are line graphs showing the induction profile of IL-6 in PBMC after in vitro stimulation with increasing concentrations of 121A and Bif 35624.
Figure 9B:
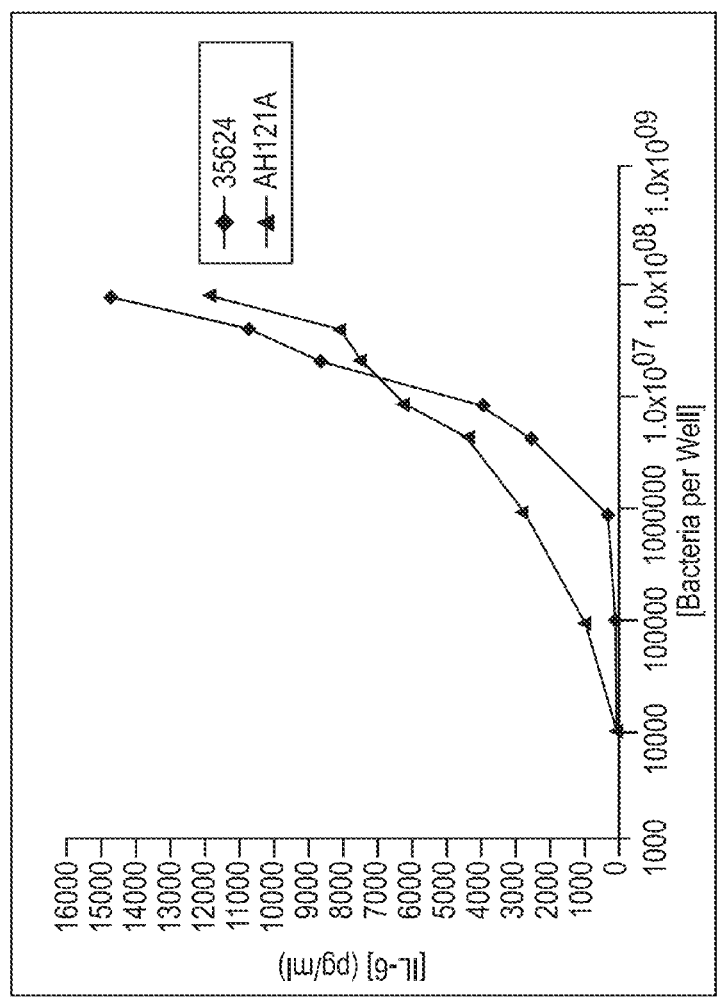
Figure 9C:
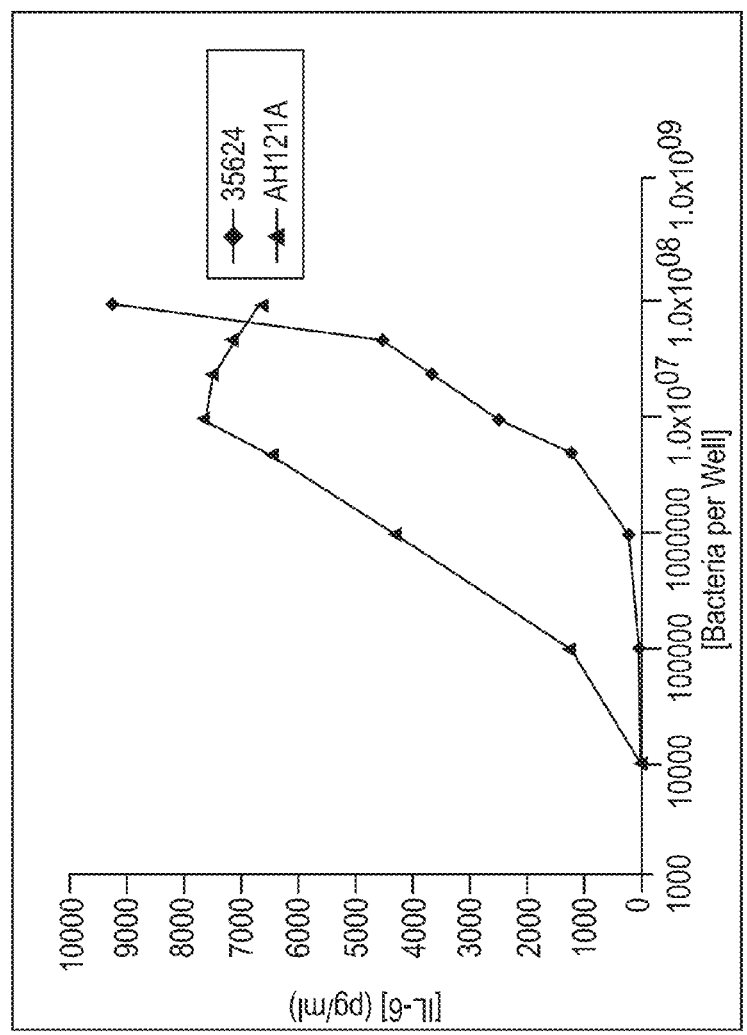
Figure 9D:
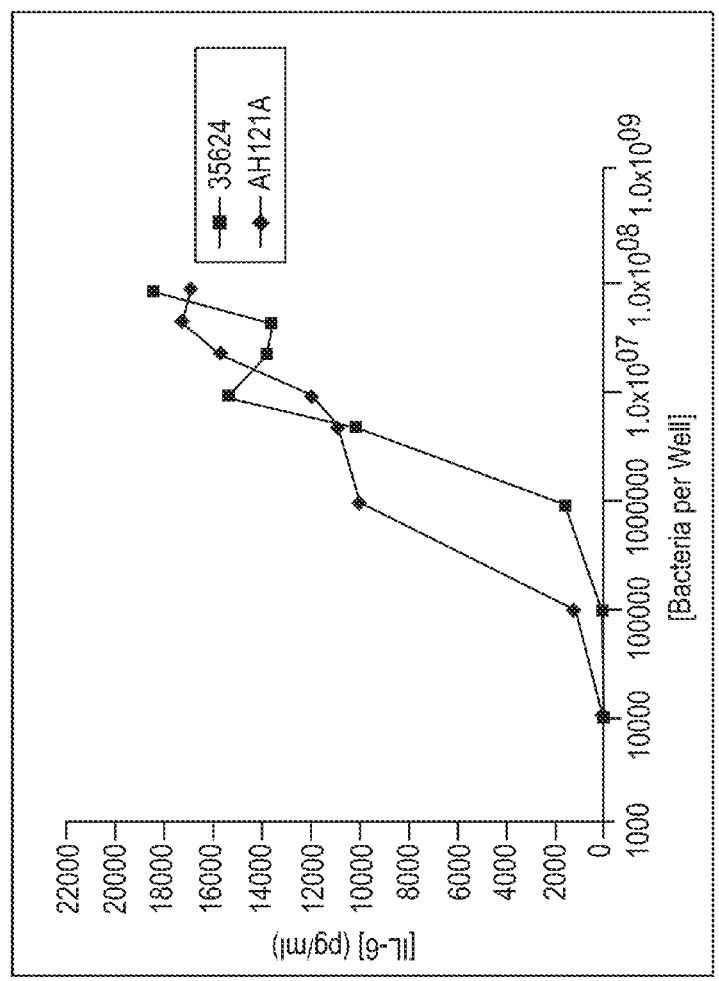
Figure 10A:
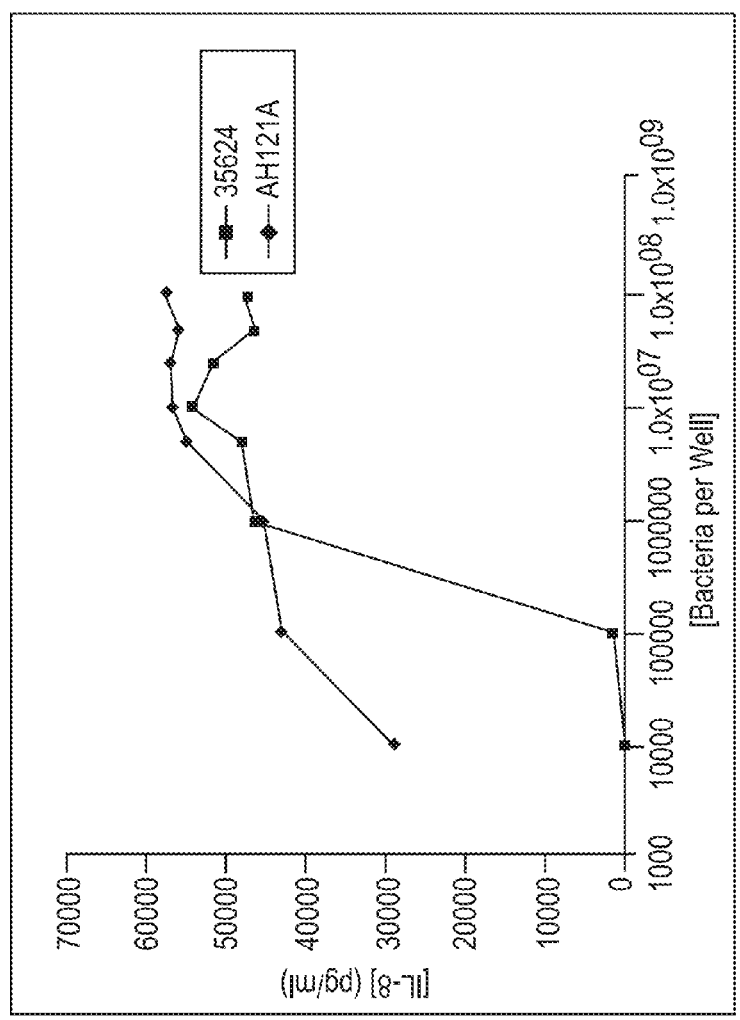
FIG. 10 A to D are line graphs showing the induction profile of IL-8 in PBMC after in vitro stimulation with increasing concentrations of 121A and Bif. 35624.
Figure 10B:
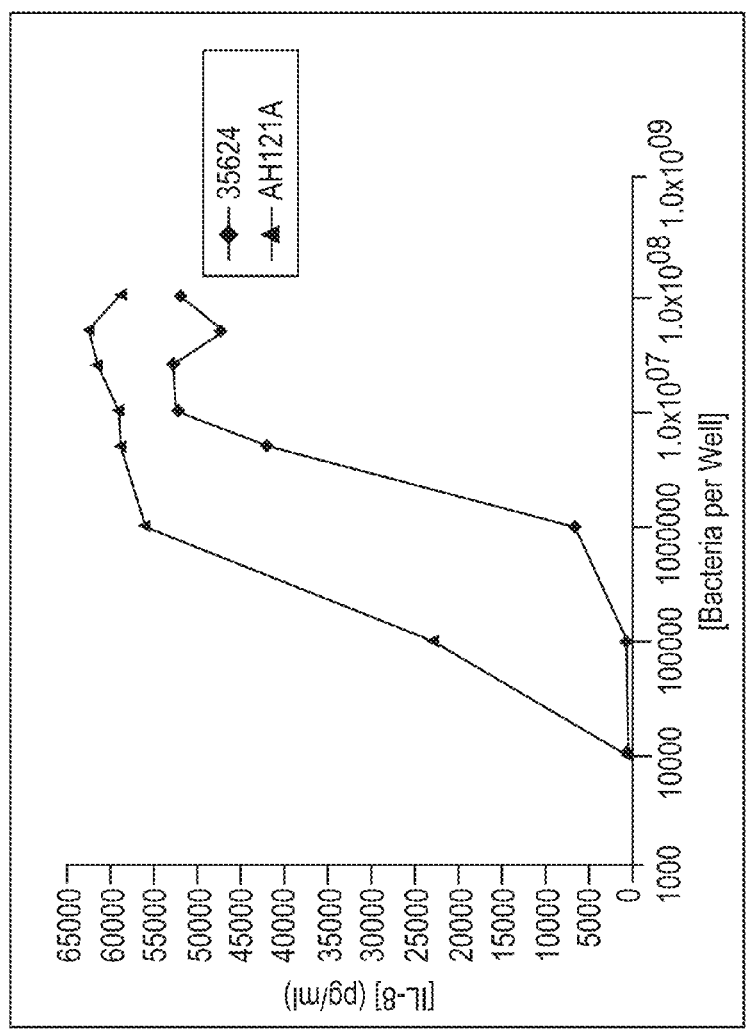
Figure 10C:
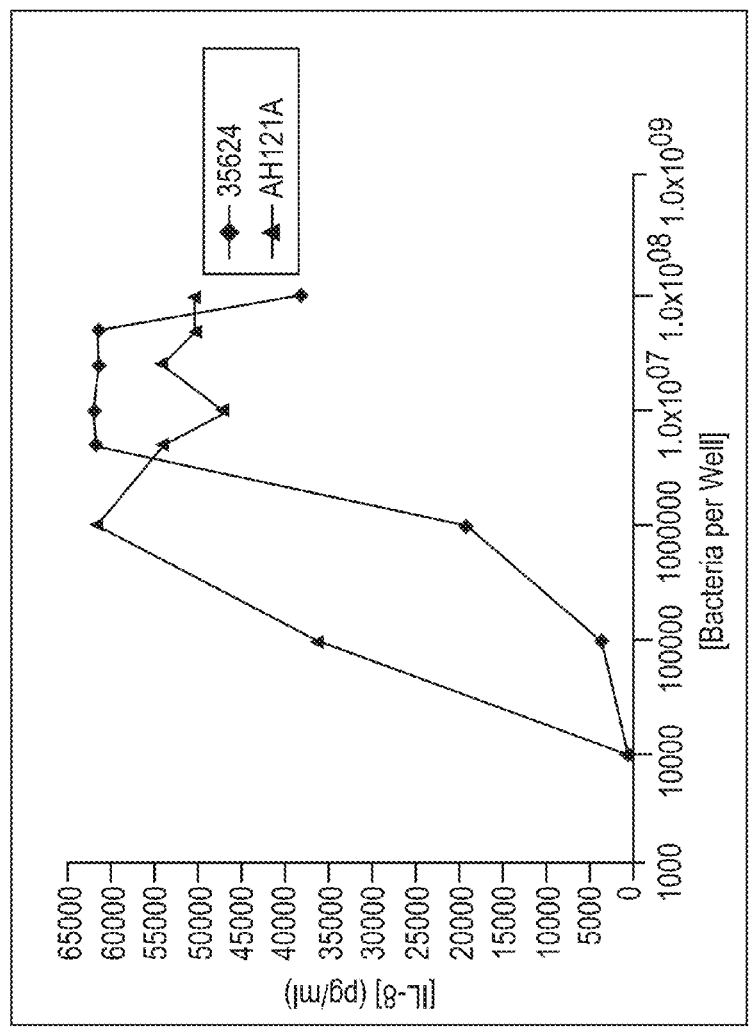
Figure 10D:
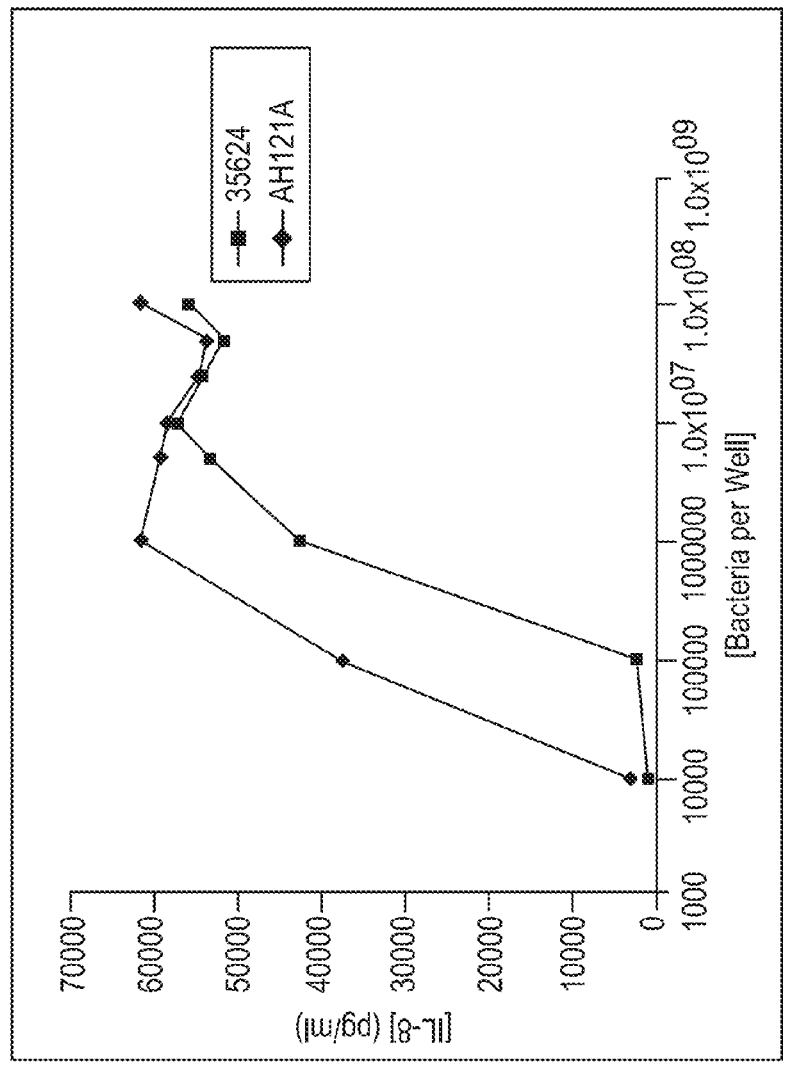
Figure 11A:
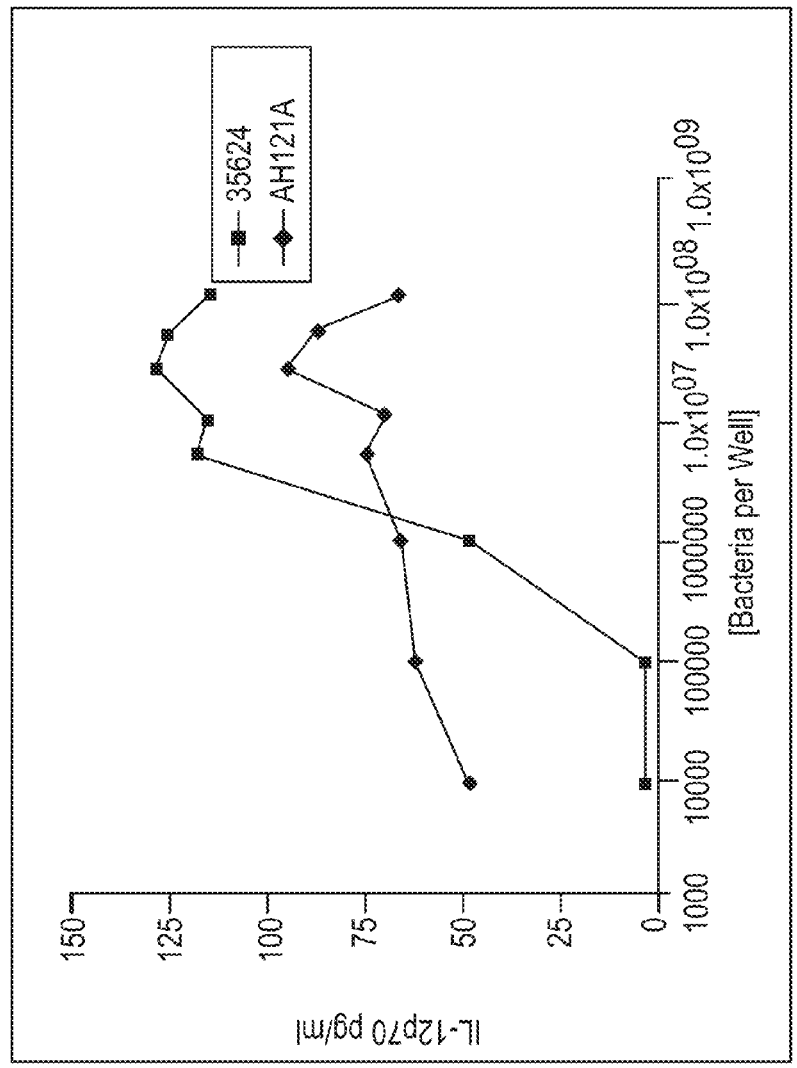
FIG. 11A to D are line graphs showing the induction profile of IL-12 p70 in PBMC after in vitro stimulation with increasing concentrations of 121A and Bif. 35624.
Figure 11B:
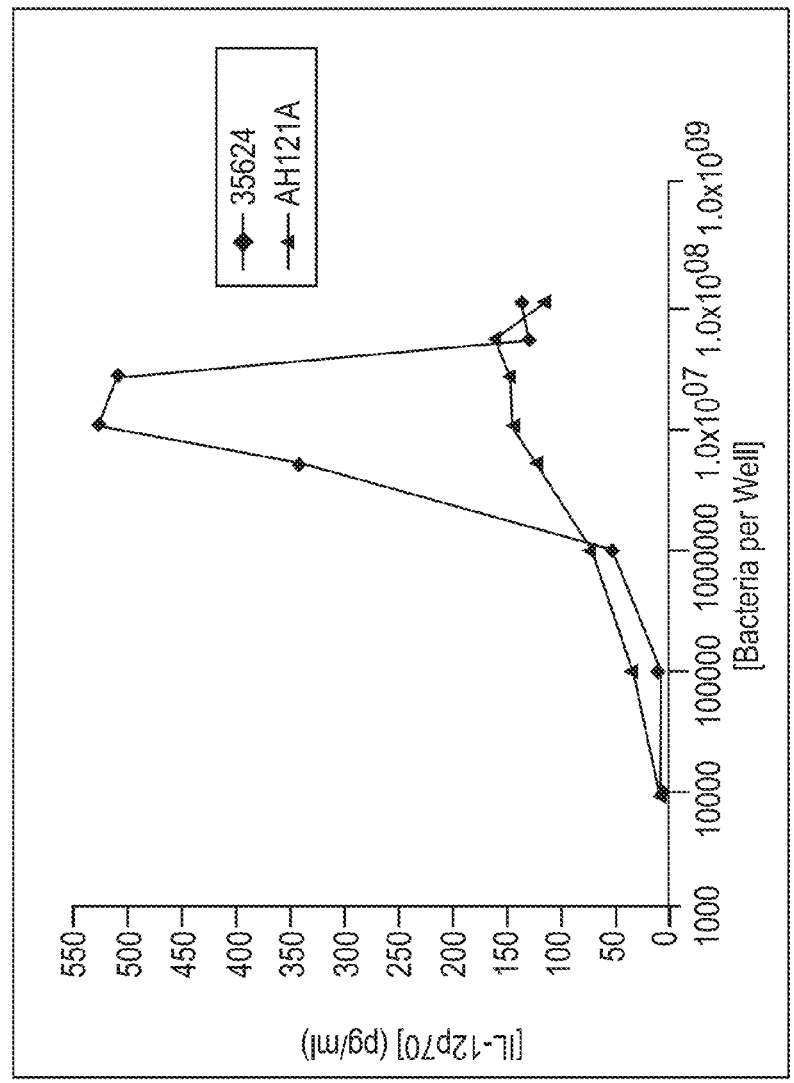
Figure 11C:
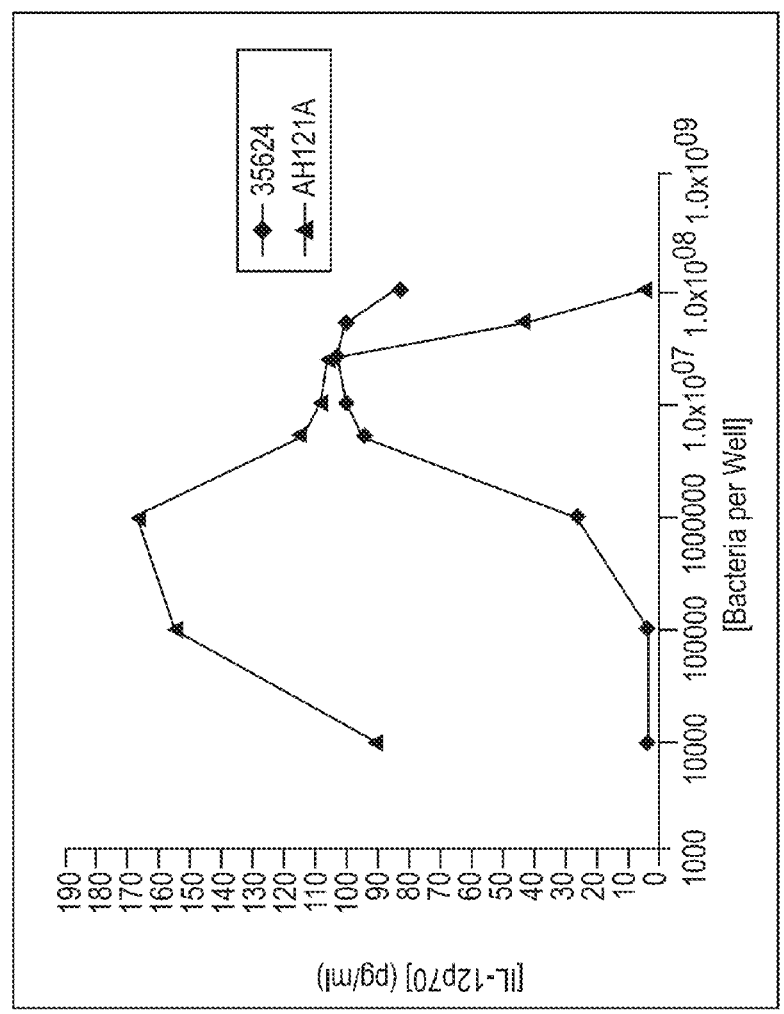
Figure 11D:
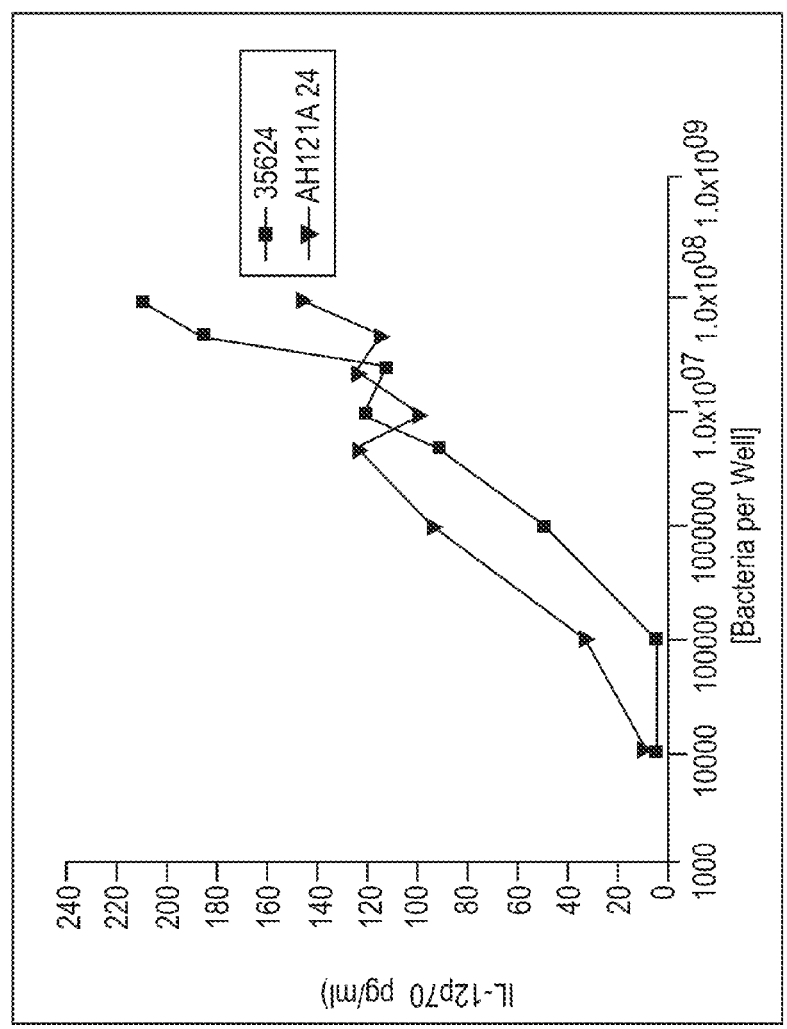
Figure 12A:
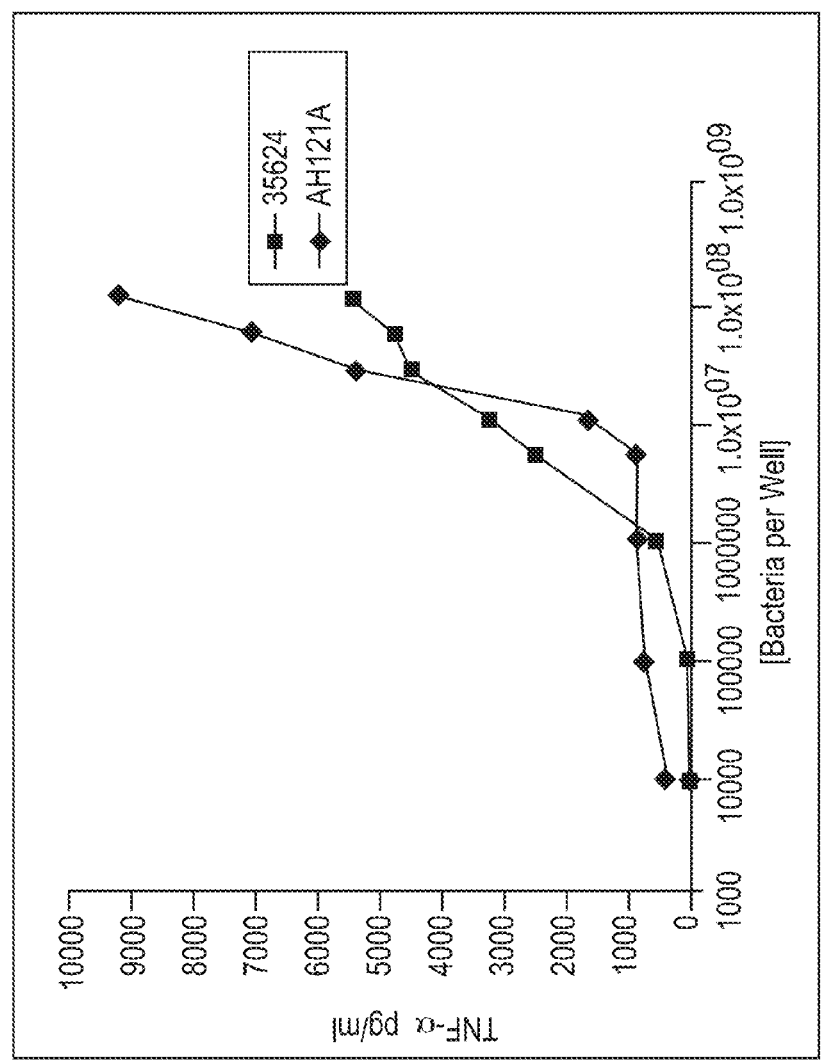
FIG. 12 A to E are line graphs showing the induction profile of TNF-α in PMBC after in vitro stimulation with increasing concentrations of 121A and Bif. 35624.
Figure 12B:
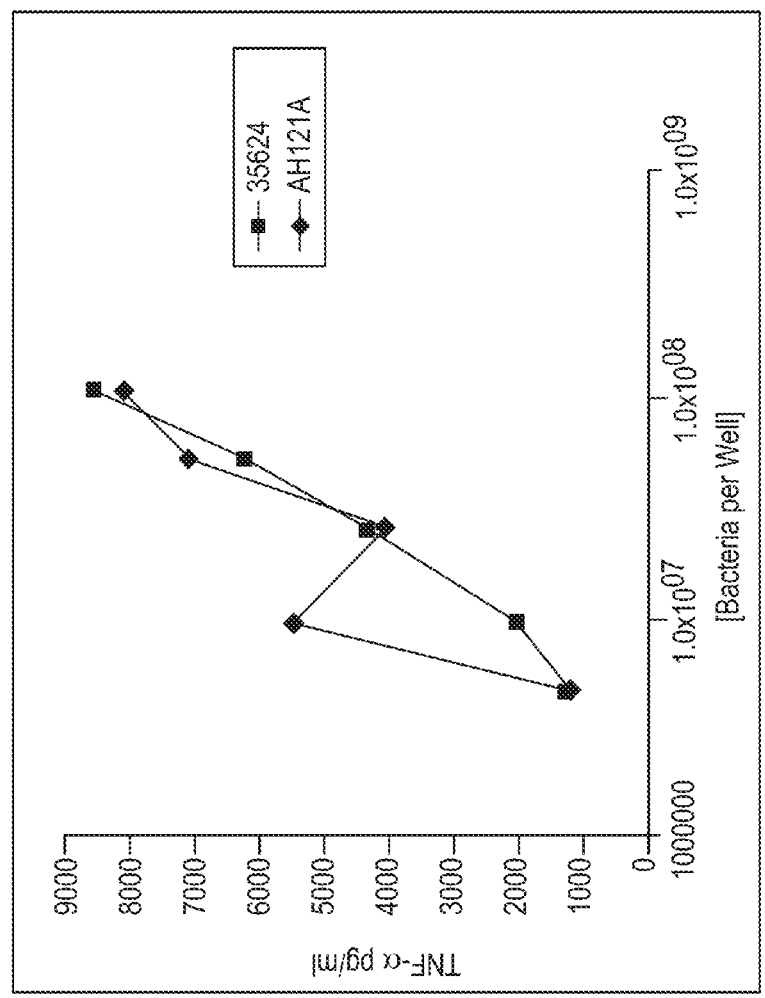
Figure 12C:
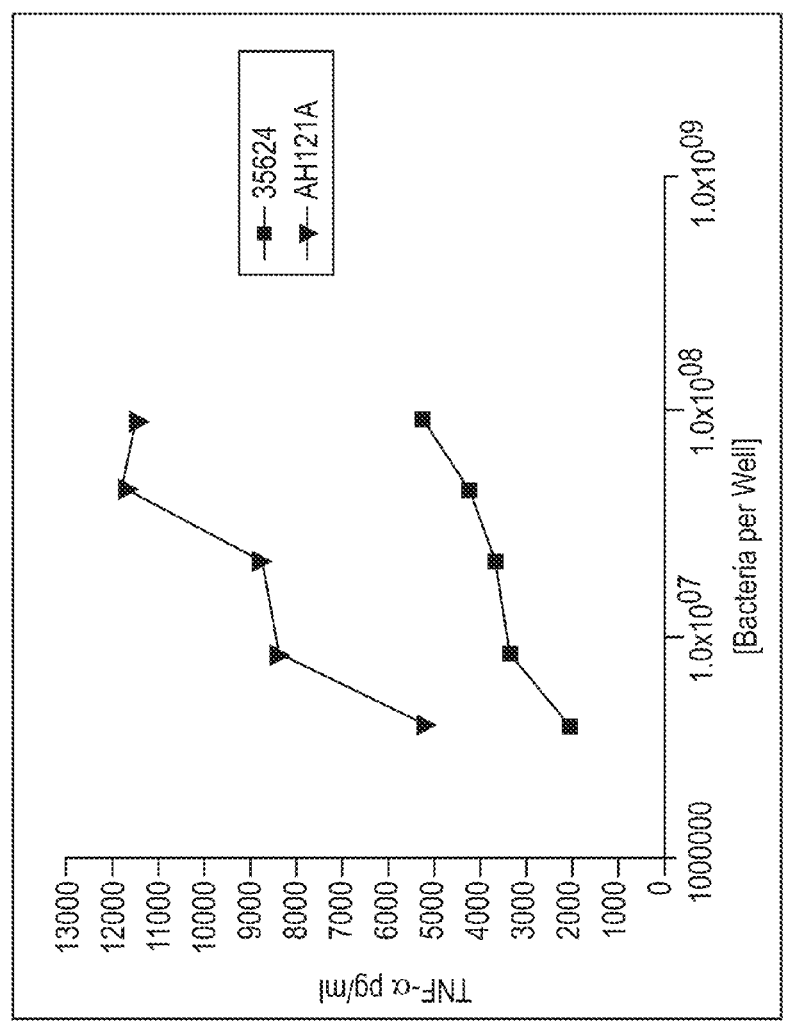
Figure 12D:
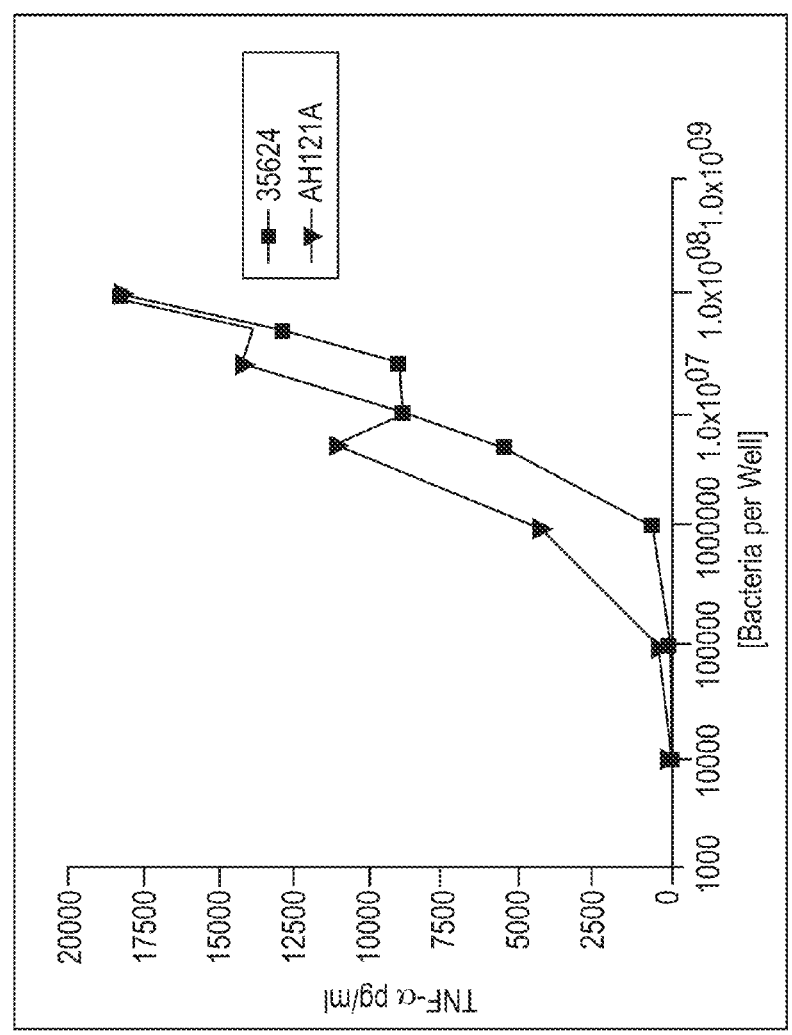
Figure 12E:
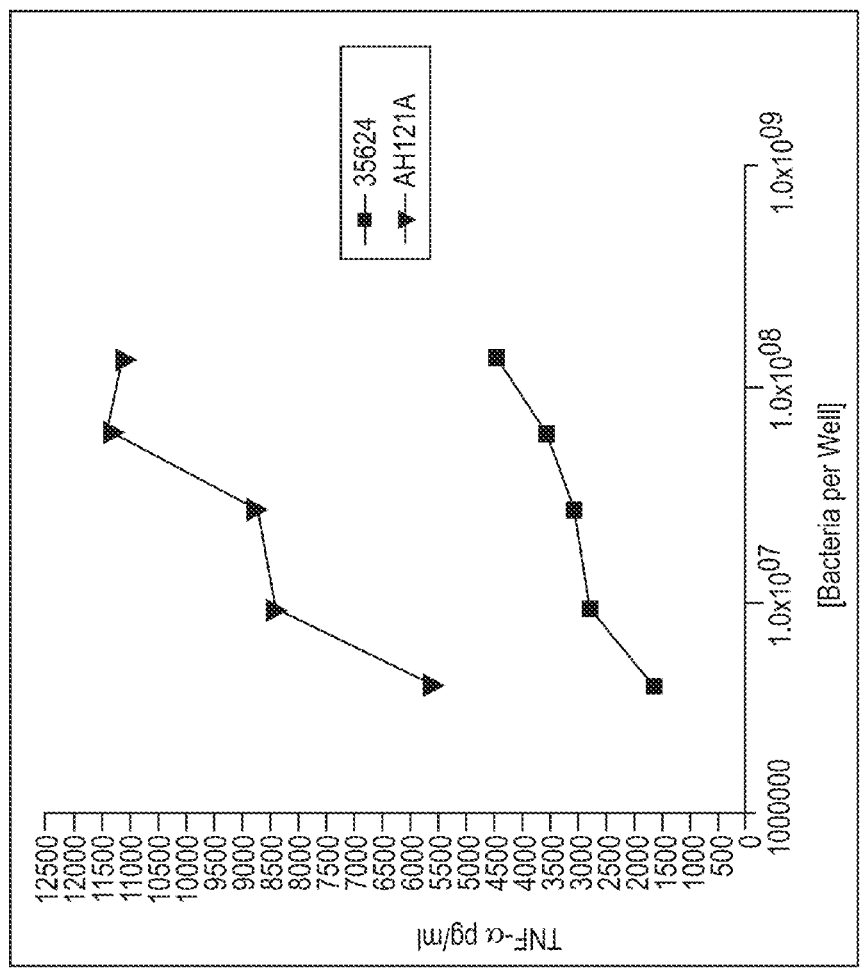

IL-10 secretion from in vitro cultured peripheral blood mononuclear cells (PBMCs) was determined 48 hours after co-incubation with each bacterial strain. The strains induced IL-10 secretion with similar IL-10 levels being noted for AHF121A and 35624. (FIGS. 4 to 6).

Example 6

Bif. AH121a has Immunomodulatory Activity when Co-Incubated with Human Immune System Cells In Vitro, Different to that of Bif. AH35624

Materials & Methods

*Bifidobacterium longum* infantis strain UCC35624 (B624) and *Bifidobacterium longum* strain 121a is assayed using a PBMC cytokine induction assay. Bacteria are prepared for co-culture experiments in the following formats. Bacteria are grown under anaerobic conditions at 37° C. in Difco MRS Media and harvested just after entering into stationary phase. Freeze dried powders are generated for each of these bacteria and stored at −80° C. in pre-aliquoted 100 mg vials. Immediately prior to their use, one aliquot of each strain is removed from the freezer and allowed to reach room temperature. Each strain is washed 3 times in 10 ml ringers followed by centrifugation. A fresh vial is used on each occasion.

Direct microscopic counts are performed using a Petroff-Hausser counting chamber as per the manufacturer's instructions and washed cells normalized by cell number before addition to the PBMC assay. Bacteria (20 μl in phosphate buffered saline (PBS)) are added to each well of PBMCs to give the total number of bacteria as indicated for each experiment.

PBMC (Peripheral Blood Mononuclear Cell) Cytokine Induction Assay

Peripheral blood mononuclear cells (PBMCs) are isolated from healthy human peripheral blood using BD Vacutainer CPT tubes (BD catalog 362761), as per the manufacturer's instructions. PBMCs are washed and resuspended in Dulbecco's Modified Eagle Medium-Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs are incubated ($2\times10^5$ cells per well) in flat-bottomed 96-well plates and 20 μL of a bacterial suspension (with concentration ranges between $1\times10^{6-8}$ CFU/mL) added. Up to 6 different amounts of bacteria are tested: 2.5E+08, 1.0E+08, 5.0E+07, 2.5E+07, 1.0E+07, and 1.0E+06. A no-bacteria control also is run. All assays are done in triplicate. After a 2-day incubation at 37° C., the plates were spun at 300×g, and the supernatants were removed and stored frozen at −80° C. until analysis. PBMCs are co-incubated with bacteria for 48 hours at 37° C./5% $CO_2$ in an incubator. Cytokines in the culture supernatants are assayed using a 96-well assay kit from Meso Scale Discovery (Gaithersburg, Md.; catalog K15008B-1). Human Interleukin 1 beta (Il-1β), Human Interleukin 6 (Il-β), Human Interleukin 8 (Il-8) Human Interleukin 10 (Il-10), Human Interleukin 12p70 (Il12p70), Human Interferon-gamma (IFN-γ), Human Tumor Necrosis Factor alpha (TNFα) and Human G-CSF are quantitated and reported as picograms per millilitre (pg/mL). Each sample is assayed in 3-5 replicates (A to E).

Results

*Bifidobacterium longum* infantis strain UCC35624 (B624) and *Bifidobacterium longum* strain 121a are assayed for immuno-modulation using a PBMC cytokine induction assay, to generate extended dose response curves with up to 6 different amounts of bacteria tested: 2.5E+08, 1.0E+08, 5.0E+07, 2.5E+07, 1.0E+07, and 1.0E+06. Supernatants are assayed for a range of cytokines, including IL-1β, -6, -8, -10 and -12, TNF-α, IFN-γ □ and G-CSF□. Cytokine measurement is represented as the average (+/−SEM) from up to 5 individual donors (A to E).

By comparison with 35624, strain 121a exhibited a very similar pattern for the induction of most cytokines including IL-10, but quite a different pattern and increased production of IL-6 and IL-8.

IL-10: Incubation with 121a induces a dose-responsive increase in the anti-inflammatory cytokine IL-10 in PBMC after in vitro stimulation (FIG. 7). Induction of IL-10 is qualitatively and quantitatively similar to incubation with 35624. Maximal induction of IL-10 does not appear to be met with up to $1.0\times10^9$ bacteria per well.

IL-1β: Incubation with 121a induces a dose-responsive increase in the pro-inflammatory cytokine IL-1β in PBMC after in vitro stimulation (FIG. 8). Induction of IL-1β is qualitatively and quantitatively similar to incubation with 35624. Maximal induction of IL-1β does not appear to be met with up to $1.0\times10^9$ bacteria per well.

IL-6: Incubation with 121a induces a dose-responsive increase in the cytokine IL-6 in PBMC after in vitro stimulation (FIG. 9). Quantitatively the pattern is different with 121a as compared with 35624; with higher levels of IL-6 measured with 121a especially at lower doses of bacteria per well.

IL-8: Incubation with 121a induces a dose-responsive increase in the cytokine IL-8 in PBMC after in vitro stimulation (FIG. 10). Quantitatively the pattern is different with 121a as compared with 35624; with higher levels of IL-8 measured with 121a across all doses of bacteria per well.

IL-12: Incubation with 121a induces a dose-responsive increase in the pro-inflammatory cytokine IL-12 in PBMC after in vitro stimulation (FIG. 11). The pattern of modulation of IL-12 is bell-shaped with 121a and with 35624, rising to peak levels and then decreasing with higher bacterial concentrations. Quantitatively the pattern is somewhat variable for IL-12, but on balance similar with 121a as compared with 35624.

TNF-α: Incubation with 121a induces a dose-responsive increase in the pro-inflammatory cytokine TNF-α in PBMC after in vitro stimulation (FIG. 12). Induction of TNF-α is qualitatively and quantitatively similar to incubation with 35624 for 3 of 5 replicates, with higher levels of TNF-α found in 2 of 5 replicates (See C & E). Maximal induction of IL-10 appears to be met with up to $1.0\times10^8$ bacteria per well.

Figure 13A:
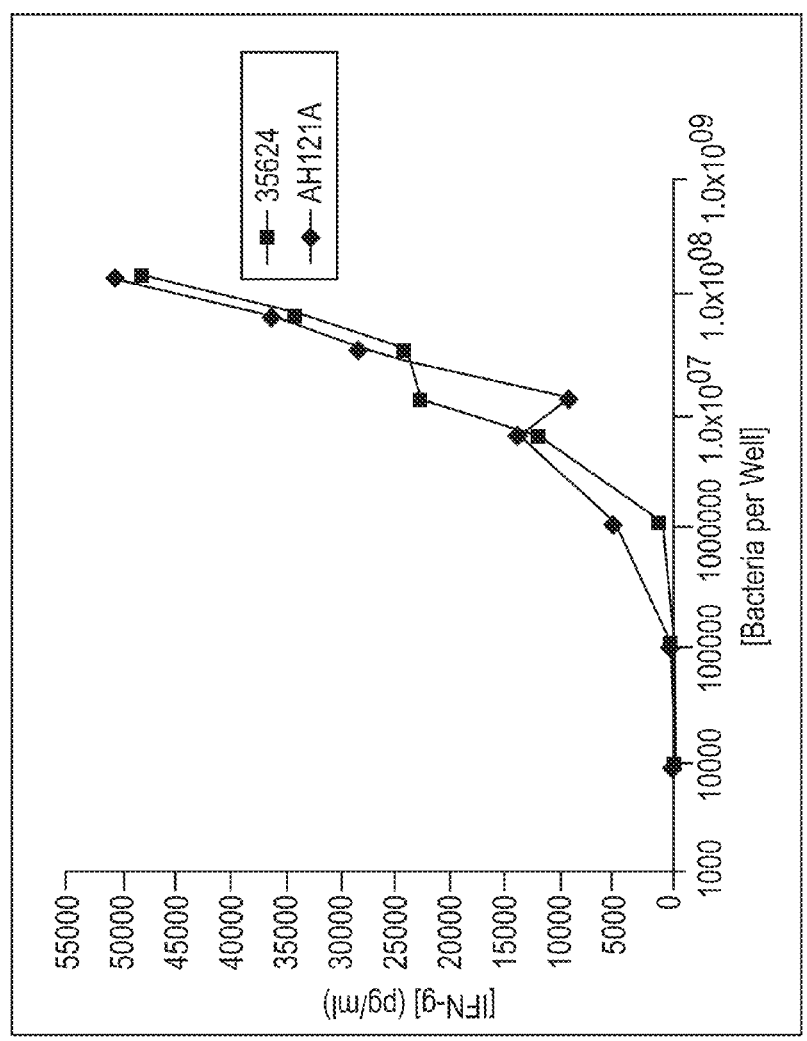
FIG. 13 A to C are line graphs showing the induction profile of IFN-γ in PMBC after in vitro stimulation with increasing concentrations of 121A and Bif. 35624.
Figure 13B:
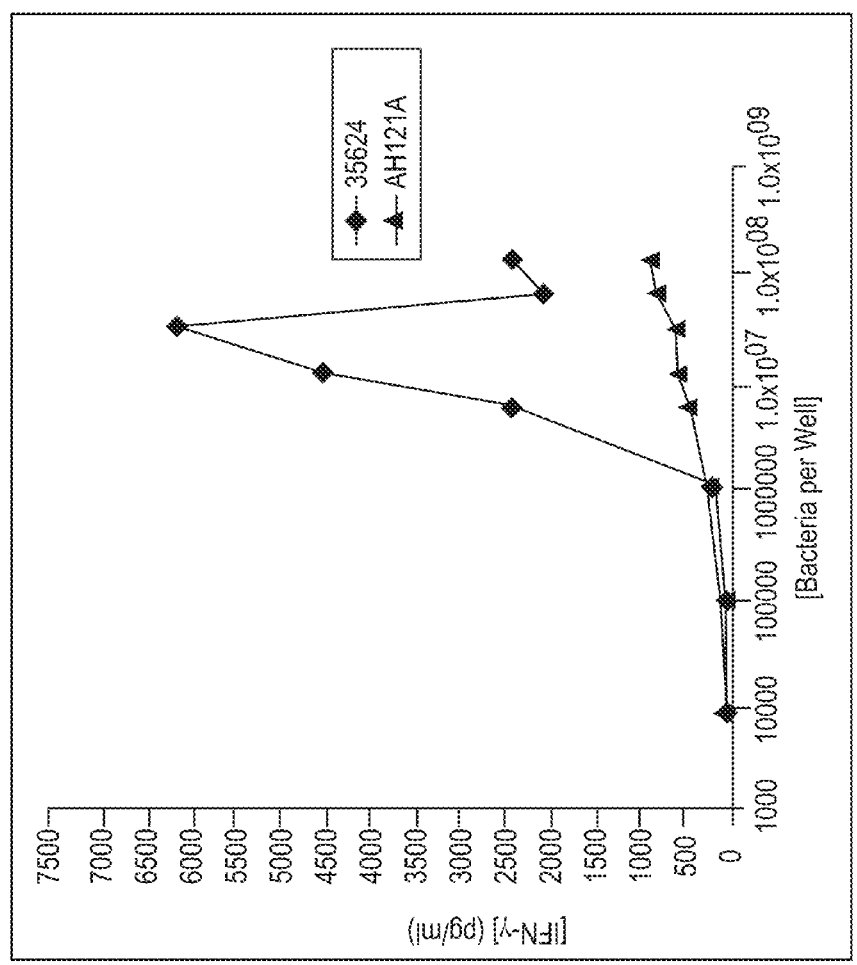
Figure 13C:
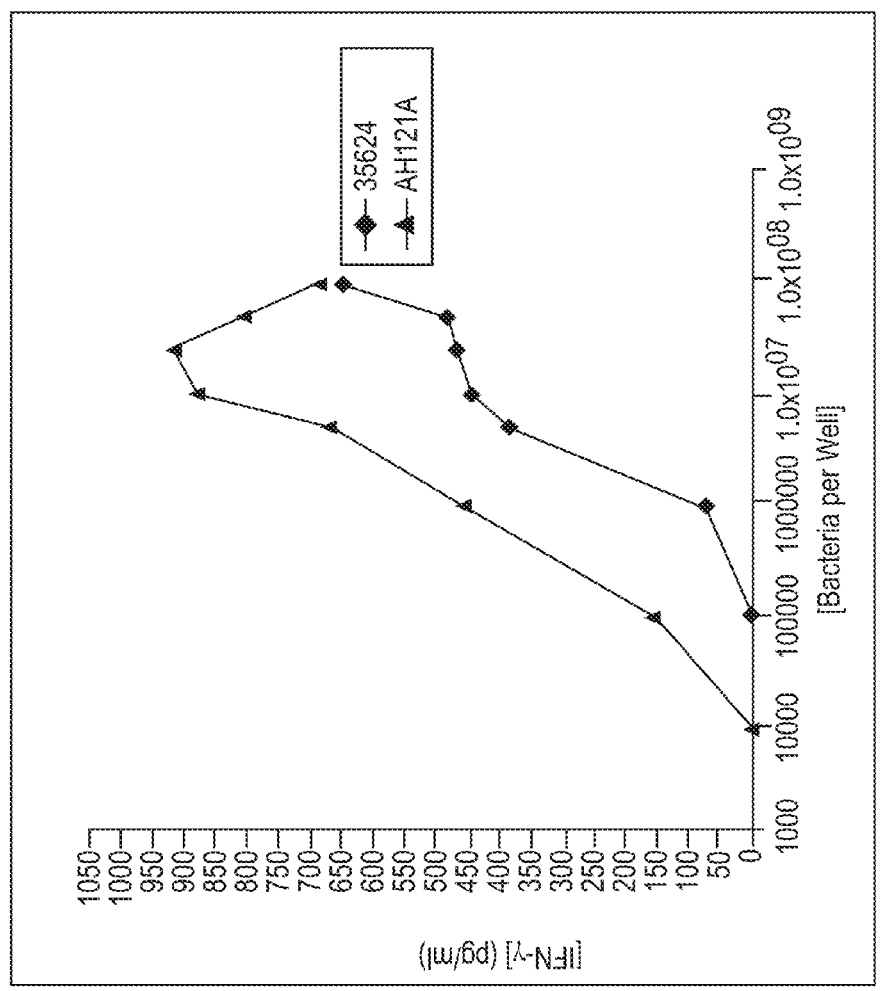
Figure 14A:
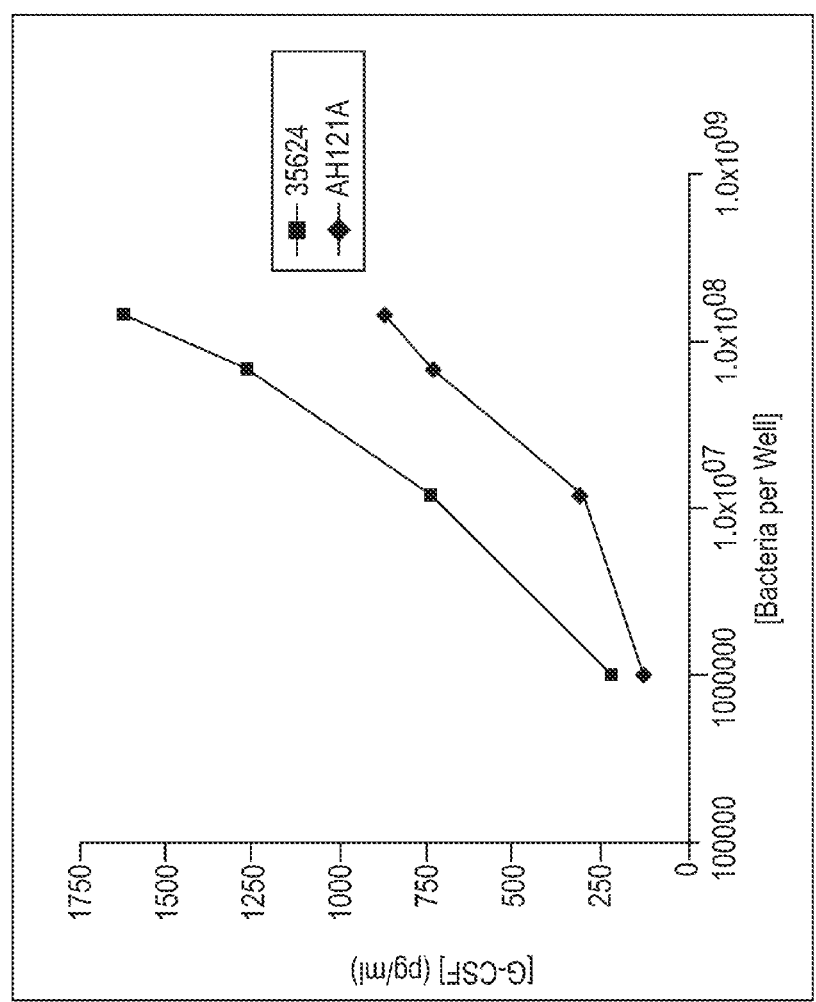
FIG. 14 A to D are line graphs showing the inductions profile of G-CSF in PBMC after in vitro stimulation with increasing concentrations of 121A and Bif. 35624.
Figure 14B:
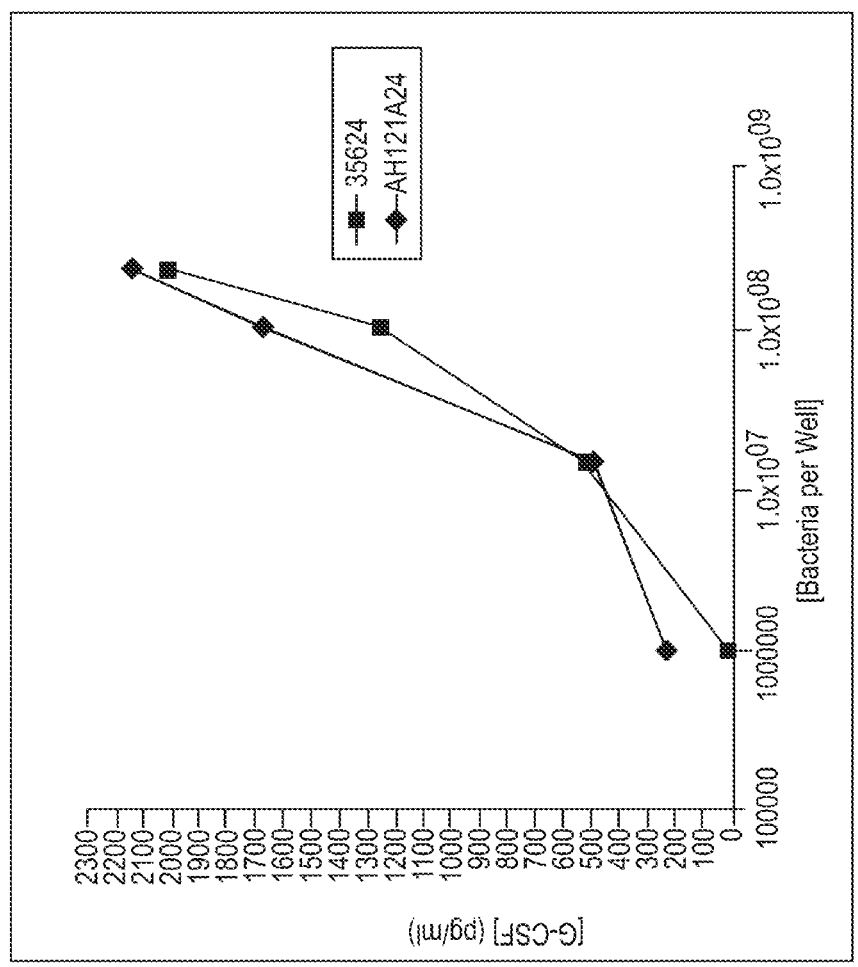
Figure 14C:
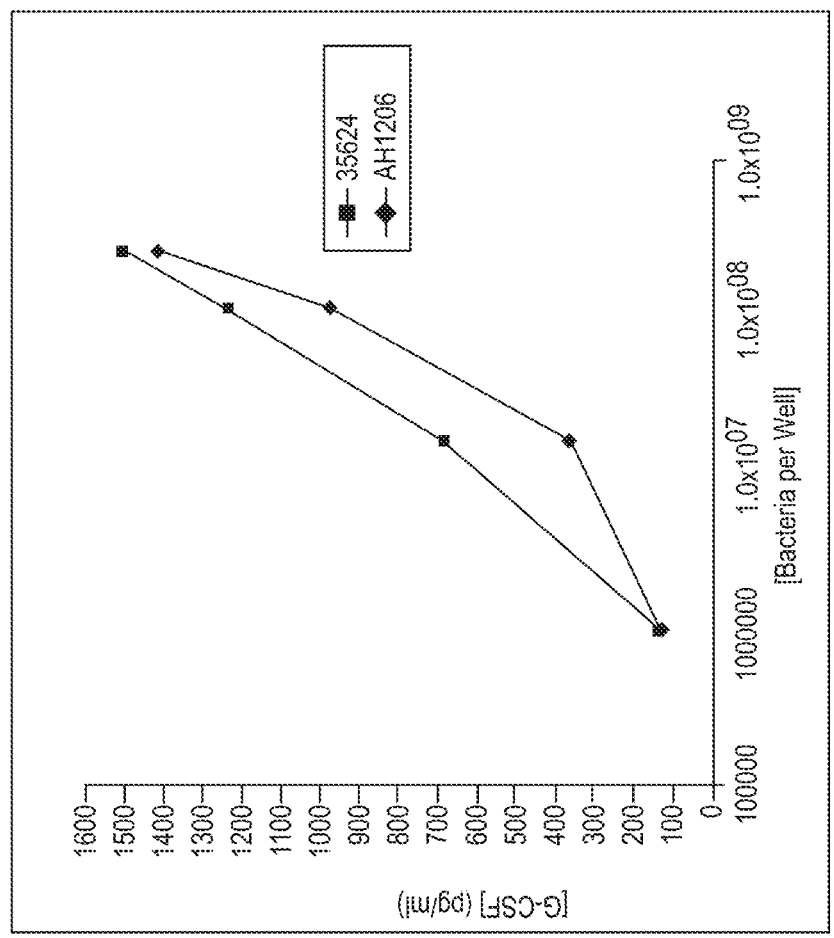
Figure 14D:
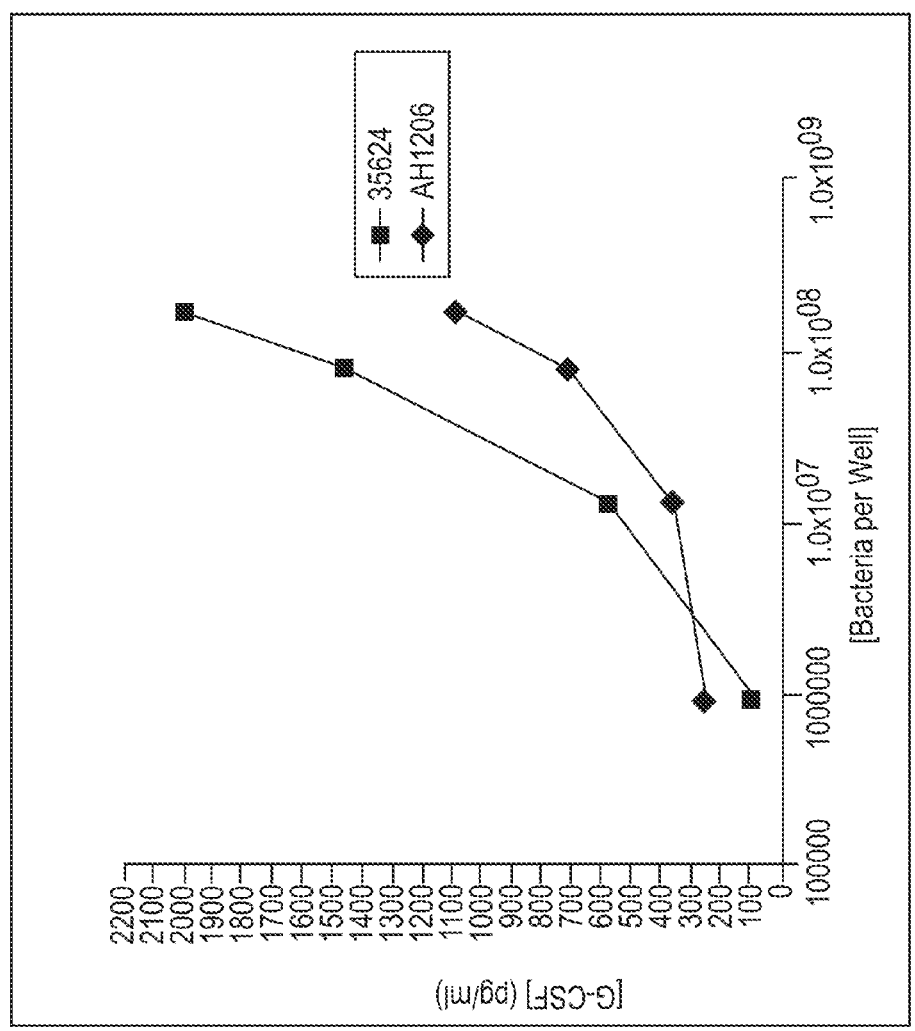

INF-γ Incubation with 121a induces a dose-responsive increase in the pro-inflammatory cytokine INF-γ in PBMC after in vitro stimulation (FIG. 13). Quantitatively the pattern is somewhat variable for INF-γ, but on balance similar with 121a as compared with 35624.

G-CSF: Incubation with 121a induces a dose-responsive increase in the cytokine G-CSF in PBMC after in vitro stimulation (FIG. 14). Induction of G-CSF is qualitatively and quantitatively similar to incubation with 35624.

Example 7

Effect of 121A on Cytokine Production by Dendritic Cells

Summary

The immune response is a tightly regulated process which normally results in protection from infection and tolerance of innocuous environmental antigens. However, in inflammatory disease, the activated immune response results in a chronic pro-inflammatory state characterized by activation of the innate immune response and expansion of polarized T cell subsets. Currently, the treatment of inflammatory disease is focussed on the suppression of key inflammatory mediators or inflammatory cell populations. However, these approaches only provide a temporary suppression of disease symptoms. Successful long-term treatment or prevention can only be provided by enhancement of the regulatory cellular processes which protect against damaging pro-inflammatory responses. *Bifidobacterium* AHF121A is a probiotic microbe that selectively stimulates IL-10 secretion from the innate immune system (i.e. dendritic cells) and induces polarization of Foxp-3 positive regulatory T cells in vitro. In vivo, IL-10 secretion and regulatory T cells are potent suppressors of aberrant inflammatory responses.

$T_{reg}$ Cells

The fundamental role for T regulatory ($T_{reg}$) cells in maintaining immune tolerance has been demonstrated in a wide range of animal models, in which the adoptive transfer or deliberate expansion of $T_{reg}$ cells was shown to prevent or cure several T-cell-mediated diseases, including allergy, asthmatic lung inflammation, autoimmune diseases and allograft rejection, by restoring immune tolerance to allergens, self antigens or alloantigens [8]. Multiple molecular mechanisms for $T_{reg}$ mediated immunosuppression have been described with secretion of IL-10 being of particular importance [9]. Absence or defective function of $T_{reg}$ cells has also been correlated with hyper IgE syndrome, hypereosinophilia and autoimmunity in humans, whereas their presence has been associated with immune tolerance [10]. Studies on the mechanisms by which immune responses to non-pathogenic environmental antigens lead to either allergy or non-harmful immunity have demonstrated that allergen-specific IL-10 producing $T_{regs}$ ($T_R1$ cells) are the dominant T-cell subset in healthy individuals [11, 12]. Repeated exposure of non-allergic healthy beekeepers to bee venom antigens during the bee keeping season represents a valuable in vivo model to ascertain mechanisms of immune tolerance to venom antigens [13]. After multiple bee stings, venom antigen-specific $T_H1$ and $T_H2$ cells switch toward IL-10-secreting $T_R1$ cells. This occurs in parallel to the suppression of cutaneous late-phase responses to allergens and inhibition of allergen-specific $T_H1$ and $T_H2$ cells. The response is observed as long as venom exposure persists and returns to initial levels within 2 to 3 months after the end of the bee keeping season.

Various strategies, which are designed to enhance $T_{reg}$ function in vivo are currently under investigation. These include the adoptive transfer of inducible or constitutive $T_{reg}$ cells and their induction by specific adjuvants or immunomodulators. These approaches are attractive compared to conventional treatments, as the antigen-specific suppressor capacity of $T_{reg}$ cells does not result in general immunosuppression and may actually lead to long-lasting antigen-specific regulation in vivo. Moreover, individual patient-specific treatments are possible with limited side effects. Many immunomodulators that have been developed or are under development, such as rapamycin, the CD80/CD86:CD28 co-stimulation blocker abatacept (Orencia; Bristol-myers Squibb), non-mitogenic anti-CD3 monoclonal antibodies, T-cell depletion and anti-tumour necrosis factor-α (TNF-α) mAbs display direct or indirect effects on $T_{reg}$ cells, which may enhance or suppress their function [14-18]. There is a selective advantage to expand a population of $T_{reg}$ cells that can target the organ (or the lymph nodes that drain the organ) by recognition of an allergen or an autoantigen expressed in inflamed organs in mouse models [19]. Thus, transfer of organ-specific $T_{reg}$ cells can be effective at suppressing ongoing disease, although those $T_{reg}$ cells do not necessarily need to recognize exactly the same autoantigen as the autoaggressive effector T cells [20]. This has implications for therapeutic strategies aimed at targeting the $T_{reg}$-cell arm of immune tolerance against allergens, autoantigens or transplantation antigens. Possibilities of adoptive transfer of $T_{reg}$ cells or small molecular compounds that induce $T_{reg}$ cells in the tissue are being investigated [19], but no double-blind, placebo-controlled studies have been reported so far. To date, allergen-SIT is the only antigen-specific approach that induces $T_{reg}$ cell production and activation in humans. Allergen-SIT induces $T_{reg}$ and IL-10-secreting $T_R1$-like cells and treatment with glucocorticoids and β2 adrenergic agonists seems to promote the number and activity of these cells [21-23]. The essential transcriptional elements regulating expression of the Foxp3 promoter have been recently reported and these will provide new targets for the development of novel therapeutics [24, 25].

Microbes as Novel Therapeutic Options

Interest in the deliberate administration of microbes or microbial metabolites for the treatment of aberrant inflammatory activity is gaining momentum. The typical microbes which are currently being examined include Bifidobacteria, Lactobacilli, non-pathogenic *E. coli* and *Bacteroides* strains [26-31]. The protective effects associated with these microbes are probably mediated by multiple mechanisms involving epithelial cells, dendritic cells and T cells. However, a common feature of these microbes, which is being increasingly reported is their ability to induce $T_{reg}$ cells. For example, encounters with a mixture of commensal microbes (VSL#3 probiotic cocktail) within the murine gut, have been shown to drive the development of mucosal $T_{reg}$ cells which is associated with attenuation of inflammation in a murine model of colitis [32]. In addition, the consumption of a *Bifidobacterium infantis* strain promotes $T_{reg}$ cell conversion and protects against LPS-induced NF-κB activation in vivo while *Lactobacillus reuteri* induces $T_{reg}$ cells which protect against an allergic airway response in mice [33, 34]. $T_{reg}$ cells are derived from the thymus but may also be induced in peripheral organs, including the gut mucosa [35, 36]. CD103+ dendritic cells within the mucosa are largely responsible for the conversion of $T_{reg}$ cells via TGF-β and retinoic acid dependent processes [37, 38]. The conversion is likely driven by gastrointestinal specific environmental factors associated with the presence of large numbers of commensal organisms. However, it is unlikely that all commensal microbes are equally effective at inducing $T_{reg}$ cells in vivo. A recent study, comparing multiple commensal organisms (*Bifidobacterium longum* AH1206, *Bifidobacterium breve* AH1205 & *Lactobacillus salivarius* AH102), has shown that *Bifidobacterium longum* AH1206 induced $T_{reg}$ cells and was also able to protect against eosinophil recruitment to the lung and blocked induction of serum IgE in murine models [39]. The other bacterial strains did not effectively induce $T_{reg}$ cells and were not able to protect against allergic inflammation in the same models. Therefore, the induction of $T_{reg}$ cells may be a critical characteristic of a healthy microbiota which is protective against the development of aberrant immunological reactivity to potential allergens. In addition to using live microbes for the treatment of allergy, another exciting approach is to identify the microbial factor(s) responsible for the beneficial effect and to use these isolated factor(s) alone. For example, polysaccharide A derived from *Bacteroides fragilis* promotes an appropriate $T_H1/T_H2$ balance in germ-free mice following presentation by mucosal dendritic cells and protects against colitis in an animal model via IL-10 secreting CD4+ T cells [29, 40]. The continued identification of new microbial compounds which induce tolerogenic dendritic cells and $T_{reg}$ activity will undoubtedly lead to novel therapeutic molecules for assessment in clinical studies.

Differentiation and Maturation of Dendritic Cells

Human monocytes were isolated from blood using a combination of Ficoll density centrifugation and cell separation using CD14-specific antibody coated magnetic microbeads (MiltentyiBiotec). The purity of isolated CD14+ cell fraction was greater than 90% in all experiments. To generate immature DC (iDCs), the purified CD14+ cells were cultured for 5 days in the presence of IL-4 (R&D systems) and GM-CFS (R&D systems) to differentiate into myeloid dendritic cells. At day 6 the cells were left unstimulated (iDCs) or were stimulated with LPS (1 mg/mL) $5\times10^5$ MDDCs were stimulated with or bacterial cells for 24 hours. *B. longum* AHF121A strain s (10:1 bacteria to DC ratio ($5\times10^6$), 1:1 bacteria to D C ratio ($5\times10^5$) for 24 hours. As anticipated, as a consequence of the application of antibiotics, no bacterial growth was observed during this period. At this time supernatants were isolated and analysed for IL-10 and IL-12p70 levels using the Luminex multiplex platform.

Isolation of Human CD4+ T Cells and Co-Culture with DCs

PBMCs were isolated by centrifugation of buffy coats on Lymphoprep gradients. CD4+ T cells were separated using negative selection affinity columns (R&D Systems), according to the manufacturer's instructions. After separation, the T cells were washed and resuspended in RPMI 1640culture medium supplemented with 10% heat-inactivated foetal bovine serum, 100 IU/mL penicillin, 100 µg/mL streptomycin, and 2 mmol/L L-glutamine. Purified CD4+ Tcells ($1\times10^6$/mL) were stimulated by the combination of immobilized anti-CD3 (1 µg/mL) and soluble anti-CD28 (5 µg/mL) mAbs (Pharmingen). Subsequently, purified CD4+ T cells were incubated with the above DCs. After 48 h of CD4+ T cells were permeabilised and stained for CD25 and Foxp-3. Cells were assessed using flow cytometry.

The results show that AHF121A stimulated dendritic cells drive the polarisation and/or expansion of the regulatory T cell subset which expresses CD25 and Foxp-3.

Probiotics have a Different Ability to Induce Cytokine Production by DCs

Figure 15:
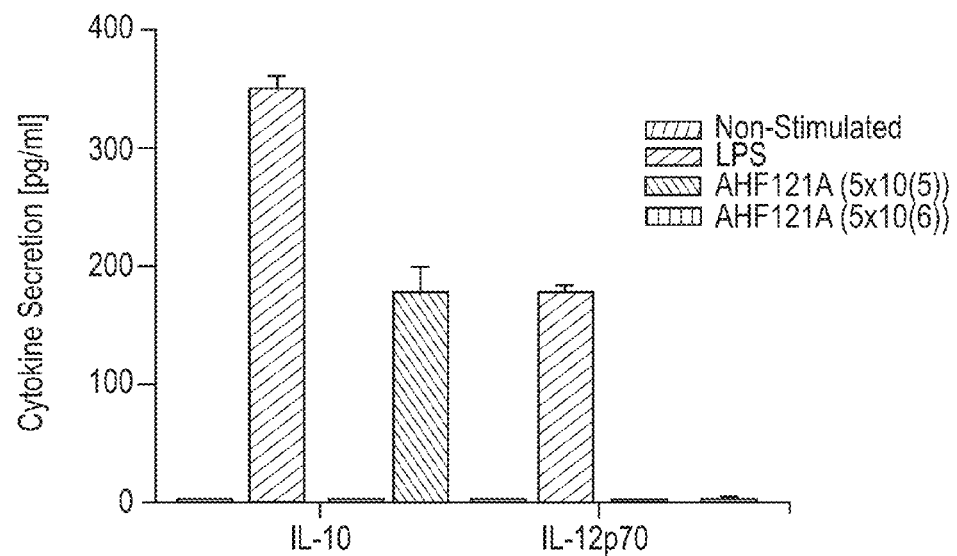
FIG. 15 is a bar chart showing the effect of 121A on the secretion of IL-10 and IL-12 p70 by human myeloid-type dendritic cells.
Figure 16:
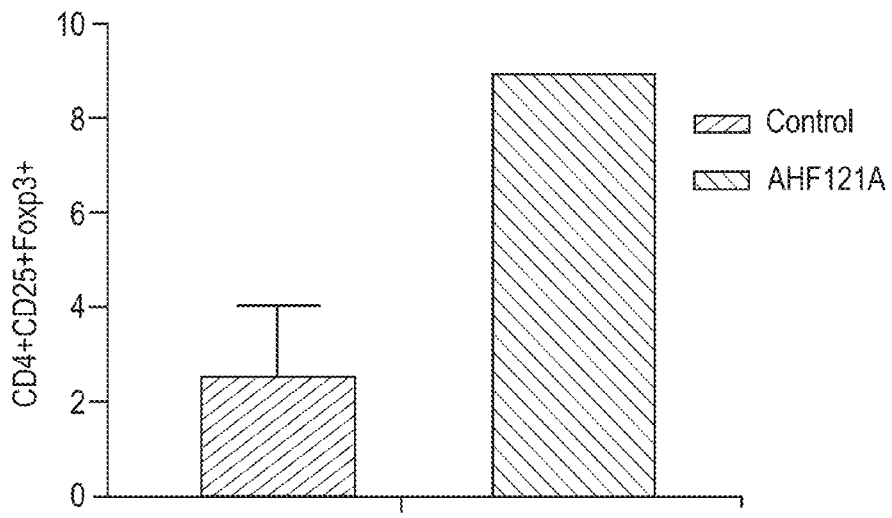
FIG. 16 is a bar chart showing the effect of 121A on human naïve CD4+ Tcells.

The type of cytokines released can have an impact on T cell polarization. Therefore, we analyzed the production of IL-12p70, and IL-10 by MoDCs after 24 h treatment with bacteria, as above. LPS was a strong inducer of all of the tested cytokines, while the AHF121A elicited a differential cytokine release (FIG. 15). AHF121A induced lower levels of IL-10 when compared to LPS but did not induce a detectable level of IL-12p70. Thus AHF121A was displaying a reduced inflammatory potential The Difference in Cytokine Production Reflects Different T Cell Polarizing Ability Cytokine release by DCs is important to drive the polarization of T cells towards Th1, Th2, Th17 or T regulatory cells. Given the differences observed in cytokine production we further tested whether MDDCs generated by AHF121A have the potential to induce Foxp3+ Tregs. DCs were incubated with AHF121A for 5 days and then cocultured with highly purified allogeneic naive CD4+ T cells. The CD4+ Foxp3+ Treg population was then analyzed by FACS. The results show that AHF121A stimulated dendritic cells drive the polarisation and/or expansion of the regulatory T cell subset which expresses CD25 and Foxp-3. (FIG. 16)

We postulate that AHF121A generated tolerogenic DCs, which, in turn, induced generation of CD4+Foxp3+ Tregs. Indeed, we demonstrated that MDDCs cultured with AHF121A could convert CD4+CD25− T cells into CD4+ CD25−Foxp3+ T cells. In summary AHF121A exerted potent immunomodulatory effects by up-regulating or potentiating the generation of Tregs by MDDCs in vitro. The results present evidence of the generation of CD4+CD25−Foxp3+ Tregs in response to AHF121A in vitro, an effect that may be therapeutically useful for the modulation of inflammatory immune disorders in vivo. (FIG. 16)

It has been shown previously that some probiotics (i.e. *L. casei* and reuteri) can induce the development of T regulatory cells (32, 41, 42). *Bifidobacterium* AH1206 was shown to mediate the potent activation of the T regulatory cells in 3 different animal models. In addition, consumption of *Bifidobacterium* AH1206 protected against eosinophil recruitment to the lung and blocked the induction of serum IgE. Here it is postulated that that T regulatory cells play an important role in regulating allergen-specific inflammatory responses (39). Multiple studies in animal models indicate CD4 CD25 Foxp3 cells are recruited into both lungs and draining lymph nodes and can suppress allergen-induced airway eosinophillia, mucous hypersecretion and airway hyperresponsiveness (43-48).

Numerous human and animal studies now indicate that IBD results from a loss of tolerance to commensal bacteria; The Round and Mazmanian study (49) show that PSA directs the development of Tregs during protection and cure of experimental colitis. These findings are consistent with studies that show inducible IL-10 production by Foxp3$^+$ T cells is important for mediating tolerance at mucosal surfaces and preventing intestinal inflammation (49, 50).

Example 8

Example Compositions

The following are examples of dried kibble compositions comprising the probiotic Bifidobacteria of the present invention.

|  | Percentage on a Weight Basis | | | |
|---|---|---|---|---|
| Ingredient | Ex. 1 | Ex. 2 | Ex. 3 | Ex. 4 |
| Cereal grains | To 100 | To 100 | To 100 | To 100 |
| Poultry by-product meal | 43.5 | 40 | 45 | 35 |
| Poultry fat | 1.28 | 1.02 | 1.16 | 1.35 |
| Egg product | 2.4 | 2.1 | 2.5 | 2.2 |
| Chicken Liver meal | 1.0 | 1.0 | 1.0 | 1.0 |
| Brewer's dried yeast | 1.0 | 1.0 | 1.0 | 1.0 |
| Monosodium phosphate | 1.0 | 1.0 | 1.0 | 1.0 |
| Calcium carbonate | 0.8 | 0.8 | 0.8 | 0.8 |
| Potassium chloride | 0.6 | 0.6 | 0.6 | 0.6 |
| Vitamins | 0.4 | 0.4 | 0.4 | 0.4 |
| Choline chloride | 0.3 | 0.3 | 0.3 | 0.3 |
| Minerals | 0.3 | 0.3 | 0.3 | 0.3 |
| DL-Methionine | 0.1 | 0.1 | 0.1 | 0.1 |
| Sodium Chloride | 0.03 | 0.03 | 0.03 | 0.03 |
| Probiotic (1 × 10$^{10}$ cfu/g NCIMB 41675 in sunflower oil) | 1 | 0.5 | — | 0.6 |
| Probiotic (1 × 10$^{10}$ cfu/g NCIMB 41675 in sunflower oil) | — | 0.5 | 1 | 0.4 |

The following are examples of wet companion animal food compositions comprising the probiotic *Bifidobacteria longum* of the present invention.

|  | Percentage on a Weight Basis | | |
|---|---|---|---|
| Ingredient | Ex. 5 | Ex. 6 | Ex. 7 |
| Water | To 38 | To 47 | To 50 |
| Poultry Liver | To 25 | To 20 | To 15 |
| Poultry Products | 25 | 20 | 20 |

-continued

| Ingredient | Percentage on a Weight Basis | | |
|---|---|---|---|
| | Ex. 5 | Ex. 6 | Ex. 7 |
| Brewers Rice | 5 | 7 | 10 |
| Egg Product | 3 | 2.5 | 1.5 |
| Poultry Fat | 2.9 | 3.0 | 3.2 |
| Chicken Stock | 0.6 | 0.7 | 0.9 |
| Taurine | 0.1 | 0.1 | 0.1 |
| Vitamins | 0.05 | 0.1 | 0.1 |
| Minerals | 0.05 | 0.1 | 0.1 |
| Probiotic (1 × $10^{10}$ cfu/g NCIMB 41675) | 4 | 5 | 6 |

The following are examples of yoghurt supplement compositions comprising the probiotic *Bifidobacteria longum* of the present invention.

| Ingredient | Percentage on a Weight Basis | | |
|---|---|---|---|
| | Ex. 8 | Ex. 9 | Ex. 10 |
| Milk | 38 | 42 | 48 |
| Sugar | 12 | 12 | 10 |
| Modified Starch | 1.0 | 0.8 | 0.8 |
| Prebiotic | 0.25 | 0.3 | 0.5 |
| Probiotic (1 × $10^{10}$ cfu/g NCIMB 41675) | 4 | 5 | 6 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

References

1. McCracken V. J. and Gaskins H. R. Probiotics and the immune system. In: *Probiotics a critical review*, Tannock, G W (ed), Horizon Scientific Press, U K. 1999, p. 85-113.
2. Savage D. C. Interaction between the host and its microbes. In: *Microbial Ecology of the Gut*, Clark and Bauchop (eds), Academic Press, London. 1977, p. 277-310.
3. Kagnoff M. F. Immunology of the intestinal tract. *Gastroenterol*. 1993; 105 (5): 1275-80.
4. Lamm M. E. Interaction of antigens and antibodies at mucosal surfaces. *Ann. Rev. Microbiol*. 1997; 51: 311-40.
5. Raychaudhuri S., Rock K L. Fully mobilizing host defense: building better vaccines. *Nat biotechnol.*, 1998; 16: 1025-31.
6. Tomomatsu, H. Health effects of oligosaccharides (1994) *Food Technol*. 48: 61-65.
7. Vickers et al., Comparison of fermentation of selected fructooligosaccharides and other fibre substrates by feline colonic microflora (2001) *Am. J. Vet. Res*. 61(4): 609-615.
8. Sakaguchi S, Yamaguchi T, Nomura T, Ono M. Regulatory T cells and immune tolerance. Cell 2008; 133:775-87.
9. Taylor A, Akdis M, Joss A, Akkoç T, Wenig R, Colonna M, Daigle I, Flory E, Blaser K, Akdis C A. IL-10 inhibits CD28 and ICOS costimulations of T cells via src homology 2 domain-containing protein tyrosine phosphatase 1. J Allergy Clin Immunol 2007; 120:76-83.
10. Chatila T A. Role of regulatory T cells in human diseases. J Allergy Clin Immunol 2005; 116:949-59.
11. Akdis M. Healthy immune response to allergens: T regulatory cells and more. Curr Opin Immunol 2006; 18:738-44.
12. Akdis M, Verhagen J, Taylor A, Karamloo F, Karagiannidis C, Crameri R, Thunberg S, Deniz G, Valenta R, Fiebig H, Kegel C, Disch R, Schmidt-Weber C B, Blaser K, Akdis C A. Immune responses in healthy and allergic Individuals are characterized by a fine balance between allergen-specific T regulatory 1 and T helper 2 cells. J Exp Med 2004; 199:1567-75.
13. Meiler F, Zumkehr J, Klunker S, Rückert B, Akdis C A, Akdis M. In vivo switch to IL-10-secreting T regulatory cells in high dose allergen exposure. J Exp Med 2008; 205; 2887-98.
14. Hendrikx T K, Velthuis J H, Klepper M, van Gurp E, Geel A, Schoordijk W, Baan C C, Weimar W. Monotherapy rapamycin allows an increase of CD4(+) CD25(bright+) FoxP3(+) T cells in renal recipients. Transpl Int 2009; 22:884-91.
15. Kremer J M, Dougados M, Emery P, Durez P, Sibilia J, Shergy W, Steinfeld S, Tindall E, Becker J C, Li T, Nuamah I F, Aranda R, Moreland L W. Treatment of rheumatoid arthritis with the selective costimulation modulator abatacept: twelve□month results of a phase iib, double-blind, randomized, placebo-controlled trial. Arthritis Rheum 2005; 52:2263-71.
16. Utset T O, Auger J A, Peace D, Zivin R A, Xu D, Jolliffe L, Alegre M L, Bluestone J A, Clark M R. Modified anti-CD3 therapy in psoriatic arthritis: a phase I/I I clinical trial. J Rheumatol 2002; 29:1907-13.
17. Isaacs J D, Greer S, Sharma S, Symmons D, Smith M, Johnston J, Waldmann H, Hale G, Hazleman B L. Morbidity and mortality in rheumatoid arthritis patients with prolonged and profound therapy-induced lymphopenia. Arthritis Rheum 2001; 44:1998-2008.
18. Ehrenstein M R, Evans J G, Singh A, Moore S, Warnes G, Isenberg D A, Mauri C. Compromised function of regulatory T cells in rheumatoid arthritis and reversal by anti-TNF-α therapy. J Exp Med 2004; 200:277-85.
19. O'Connor R A, Anderton S M. Multi-faceted control of autoaggression: Foxp3+ regulatory T cells in murine models of organ-specific autoimmune disease. Cell Immunol 2008; 251:8-18.
20. Roncarolo M G, Battaglia M. Regulatory T-cell immunotherapy for tolerance to self antigens and alloantigens in humans. Nature Rev Immunol 2007; 7:585-98.
21. Peek E J, Richards D F, Faith A, Lavender P, Lee T H, Corrigan C J, Hawrylowicz C M. Interleukin-10-secreting 21. "regulatory" T cells induced by glucocorticoids and beta2 agonists. Am J Respir Cell Mol Biol 2005; 33:105-11.
22. Karagiannidis C, Akdis M, Holopainen P, Woolley N J, Hense G, Rückert B, Mantel P Y, Menz G, Akdis C A, Blaser K, Schmidt-Weber C B. Glucocorticoids upregulate FOXP3 expression and regulatory T cells in asthma. J Allergy Clin Immunol 2004; 114:1425-33.
23. Akdis M, Akdis C A. Mechanisms of allergenspecific immunotherapy. J Allergy Clin Immunol 2007; 119:780-91.
24. Klunker S, Chong M M, Mantel P Y, Palomares O, Bassin C, Ziegler M, Rückert B, Meiler F, Akdis M, Littman D R, Akdis C A. Transcription factors RUNX1 and RUNX3 in the induction and suppressive function of Foxp3+ inducible regulatory T cells. J Exp Med 2009; 206:2701-15.
25. Mantel P Y, Kuipers H, Boyman O, Rhyner C, Quaked N, Rückert B, Karagiannidis C, Lambrecht B N, Hendriks R W, Crameri R, Akdis C A, Blaser K, Schmidt-Weber C B. GATA3-driven Th2 responses inhibit TGF-β 1-induced FOXP3 expression and the formation of regulatory T cells. PLoS Biol 2007; 5:e329.
26. van der Kleij H, O'Mahony C, Shanahan F, O'Mahony L, Bienenstock J. Protective effects of *Lactobacillus reuteri* and *Bifidobacterium infantis* in murine models for colitis do not involve the vagus nerve. Am J Physiol Regul Integr Comp Physiol 2008; 295:1131-7.
27. Sheil B, McCarthy J, O'Mahony L, Bennett M W, Ryan P, Fitzgibbon J J, Kiely B, Collins J K, Shanahan F. Is the mucosal route of administration essential for probiotic function? Subcutaneous administration is associated with attenuation of murine colitis and arthritis. Gut 2004; 53:694-700.
28. McCarthy J, O'Mahony L, O'Callaghan L, Sheil B, Vaughan E E, Fitzsimons N, Fitzgibbon J, O'Sullivan G C, Kiely B, Collins J K, Shanahan F. Double blind, placebo controlled trial of two probiotic strains in interleukin 10 knockout mice and mechanistic link with cytokine balance. Gut 2003; 52:975-80.
29. O'Mahony L, Feeney M, O'Halloran S, Murphy L, Kiely B, Fitzgibbon J, Lee G, O'Sullivan G, Shanahan F, Collins J K. Probiotic impact on microbial flora, inflammation and tumour development in IL-10 knockout mice. Aliment Pharmacol Ther 2001; 15:1219-25.
30. Mazmanian S K, Round J L, Kasper D L. A microbial symbiosis factor prevents intestinal inflammatory disease. Nature 2008; 453:620-5.
31. Grabig A, Paclik D, Guzy C, Dankof A, Baumgart D C, Erckenbrecht J, Raupach B, Sonnenborn U, Eckert J, Schumann R R, Wiedenmann B, Dignass A U, Sturm A. *Escherichia coli* strain Nissle 1917 ameliorates experimental colitis via toll-like receptor 2- and toll-like receptor 4-dependent pathways. Infect Immun 2006; 74:4075-82.
32. Di Giacinto C, Marinaro M, Sanchez M, Strober W, Boirivant M. Probiotics Ameliorate Recurrent Th1-Mediated Murine Colitis by Inducing IL-10 and IL-10-Dependent TGF-β Bearing Regulatory Cells. J Immunol 2005; 174:3237-46.
33. O'Mahony C, Scully P, O'Mahony D, Murphy S, O'Brien F, Lyons A, Sherlock G, MacSharry J, Kiely B, Shanahan F, O'Mahony L. Commensal-Induced Regulatory T Cells Mediate Protection against Pathogen-Stimulated NF-κB Activation. PLOS Pathogens 2008; 4:e1000112.
34. Karimi K, Inman M D, Bienenstock J, Forsythe P. *Lactobacillus reuteri*-induced regulatory T cells protect against an allergic airway response in mice. Am J Respir Crit Care Med 2009; 179:186-93.
35. Karim M, Kingsley C I, Bushell A R, Sawitzki B S, Wood K J. Alloantigen-induced CD25+CD4+ regulatory T cells can develop in vivo from CD25−CD4+ precursors in a thymus-independent process. J Immunol 2004; 172:923-8.
36. Chen W, Jin W, Hardegen N, Lei K J, Li L, Marinos N, McGrady G, Wahl S M. Conversion of peripheral CD4+ CD25− naive T cells to CD4+CD25+ regulatory T cells by TGF-β induction of transcription factor Foxp3. J Exp Med 2003; 198:1875-86.
37. Coombes J L, Siddiqui K R, Arancibia-Cárcamo C V, Hall J, Sun C M, Belkaid Y, Powrie F. A functionally specialized population of mucosal CD103+ DCs induces Foxp3+ regulatory T cells via a TGF-β and retinoic acid-dependent mechanism. J Exp Med 2007; 204:1757-64.
38. Sun C M, Hall J A, Blank R B, Bouladoux N, Oukka M, Mora J R, Belkaid Y. Small intestine lamina propria dendritic cells promote de novo generation of Foxp3 T reg cells via retinoic acid. J Exp Med 2007; 204:1775-85.
39. Lyons A, O'Mahony D, O'Brien F, MacSharry J, Sheil B, Ceddia M, Russell W M, Forsythe P, Bienenstock J, Kiely B, Shanahan F, O'Mahony L. Bacterial strain-specific induction of Foxp3+ T regulatory cells is protective in murine allergy models. Clin Exp Allergy 2009; in press.
40. Mazmanian S K, Liu C H, Tzianabos A O, Kasper D L. An immunomodulatory molecule of symbiotic bacteria directs maturation of the host immune system. Cell 2005; 122:107-18.
41. Foligne B, Zoumpopoulou G, Dewulf J, Ben Younes A, Chareyre F, et al. (2007) A key role of dendritic cells in probiotic functionality. *PLoS ONE* 2: e313.
42. Smits H H, Engering A, van der Kleij D, de Jong E C, Schipper K, et al. (2005) Selective probiotic bacteria induce IL-10-producing regulatory T cells in vitro by modulating dendritic cell function through dendritic cell-specific intercellular adhesion molecule 3-grabbing nonintegrin. *J Allergy Clin Immunol* 115: 1260-1267.
43. Zuany-Amorim C, Sawicka E, Manlius C et al. Suppression of airway eosinophilia by killed *mycobacterium vaccae* induced allergen-specific regulatory T-cells. *Nat Med* 2002; 8:625-9.
44. Leech M D, Benson R A, De Vries A, Fitch P M, Howie S E. Resolution of Der p1-induced allergic airway inflammation is dependent on CD4$^+$ CD25$^+$ Foxp3$^+$ regulatory cells. *J Immunol* 2007; 179:7050-8.
45. McGlade J P, Gorman S, Zosky G R et al. Suppression of the asthmatic phenotype by ultraviolet b-induced, antigen-specific regulatory cells. *Clin Exp Allergy* 2007; 37:1267-76.
46. Strickland D H, Stumbles P A, Zosky G R et al. Reversal of airway hyperresponsiveness by induction of airway mucosal CD4$^+$CD25$^+$ regulatory Tcells. *J Exp Med* 2006; 203:2649-60.
47. Wu K, Bi Y, Sun K, Xia J, Wang Y, Wang C. Suppression of allergic inflammation by allergen-DNA-modified dendritic cells depends on the induction of Foxp3$^+$ regulatory T cells. *Scand J Immunol* 2008; 67:140-51.
48. Boudousquié C, Pellaton C, Barbier N, Spertini F. CD4$^+$ CD25$^+$ T cell depletion impairs tolerance induction in a murine model of asthma. *Clin Exp Allergy* 2009; 39:1415-26.
49. Round J L, Mazmanian S K. Inducible Foxp3+ regulatory T-cell development by a commensal bacterium of the intestinal microbiota. Proc Natl Acad Sci USA. 2010 Jul. 6; 107(27):12204-9.
50. Rubtsov Y P, et al. Regulatory T cell-derived interleukin-10 limits inflammation at environmental interfaces. *Immunity.* 2008; 28:546-558.

What is claimed is:

1. A formulation which comprises *Bifidobacterium longum* strain AH121A deposited with the NCIMB under accession number 41675;
   wherein the formulation further comprises an ingestible carrier, and
   wherein the ingestible carrier is a food product selected from the group consisting of an oil suspension, a milk-based suspension, cheese, a cocoa butter based composition, a gravy and a yogurt based composition.

2. The formulation of claim 1, wherein the *Bifidobacterium longum* strain is in the form of viable cells.

3. The formulation of claim 1, wherein the *Bifidobacterium longum* strain is in the form of non-viable cells.

4. The formulation of claim 1 which further comprises a probiotic material.

5. The formulation of claim 1 which further comprises a prebiotic material.

6. A foodstuff which comprises the *Bifidobacterium longum* strain of claim 1.

7. The foodstuff as claimed in claim 6 wherein the foodstuff is a dry foodstuff.

8. The foodstuff as claimed in claim 6 wherein the foodstuff is a wet foodstuff.

9. The foodstuff of claim 6 which further comprises a probiotic material.

10. The foodstuff of claim 6 which further comprises a prebiotic material.

11. The food stuff of claim 6 wherein the foodstuff is a companion animal food.

* * * * *

SEQUENCE LISTING

<160> NUMBER OF SEQ ID NOS: 4

<210> SEQ ID NO 1
<211> LENGTH: 466
<212> TYPE: DNA
<213> ORGANISM: Bifidobacterium longum
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t

<400> SEQUENCE: 1

```
antnnagtnc gtagttctcc gaggtgtgcg ccccgcgcgt cgcatggtgc natggcggcg      60
gggttgctgg tgtggaagac gtcgttggct ttgccctgcc ggtcgtgcgg tgggtgccgg     120
ggtggtatgg atgcgctttt gggctcccgg atcgccaccc caggcttttt gcctggcgcg     180
attcgatgcc cgtcgtgcct gggggccggc cgtgtgccgg cgcgatggcg tggcggtgcn     240
tggtggcttg agaactggat agtgnacgcg agcaaaacaa gggttttttga atctttgttt    300
tgctgttgat ttcgaatcga actctattgt tcgtttcgat cgttttgtga tcatttttag     360
tgtgatgatt tgtcgtctgg gaatttgcta gaggaatctt gcggccatgc acttttgtgg     420
tgtgtgttgc ttgcaagggc gtatggtgga tgccttgcca nccaga                    466
```

<210> SEQ ID NO 2
<211> LENGTH: 466
<212> TYPE: DNA
<213> ORGANISM: Bifidobacterium longum
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t

```
<400> SEQUENCE: 2
ggcntgcggc caaacaccac aaaagtgcat ggccgcaaga attcctctag caaattccca        60
gnacgacaaa tcatcacact aaaaatgatc acaaaacgat cgaaacgaac aatagagttc       120
gattcgaaat caacagcaaa acaaagattc aaaaaccctt gttttgctcg cgtccactat       180
ccagttctca agccaccacg caccgccacg ccatcgcgcc ggcacacggc cggcccccag       240
gcacgacggg catcgaatcg cgccaggcaa aaagcctggg gtggcgatcc gggagcccaa       300
aagcgcatcc ataccacccc ggcacccacc gcacgaccgg cagggcaaag ccaacgacgt       360
cttccacacc agcaacccg ccgccatcgc accatgcgac gcgcggggcg cacaccgtcg        420
gacgaacatc cgactgaatt ctccgtagaa aggaggntnc ccagca                     466

<210> SEQ ID NO 3
<211> LENGTH: 19
<212> TYPE: DNA
<213> ORGANISM: Unknown
<220> FEATURE:
<223> OTHER INFORMATION: synthesised sequence

<400> SEQUENCE: 3
gctggatcac ctcctttct                                                    19

<210> SEQ ID NO 4
<211> LENGTH: 18
<212> TYPE: DNA
<213> ORGANISM: Unknown
<220> FEATURE:
<223> OTHER INFORMATION: synthesised sequence

<400> SEQUENCE: 4
ctggtgccaa ggcatcca                                                     18
```